US009745318B2

(12) United States Patent
Mallet et al.

(10) Patent No.: US 9,745,318 B2
(45) Date of Patent: Aug. 29, 2017

(54) FLUORESCENT RED EMITTING FUNCTIONALIZABLE CALCIUM INDICATORS

(71) Applicant: PARIS SCIENCES ET LETTRES—QUARTIER LATIN, Paris (FR)

(72) Inventors: Jean-Maurice Mallet, Vitry sur Seine (FR); Mayeul Collot, Illkirch (FR)

(73) Assignee: PARIS SCIENCES ET LETTRES—QUARTIER LATIN, Paris (FR)

( * ) Notice: Subject to any disclaimer, the term of this patent is extended or adjusted under 35 U.S.C. 154(b) by 0 days.

(21) Appl. No.: 15/039,681

(22) PCT Filed: Nov. 27, 2014

(86) PCT No.: PCT/EP2014/075766
§ 371 (c)(1),
(2) Date: May 26, 2016

(87) PCT Pub. No.: WO2015/078948
PCT Pub. Date: Jun. 4, 2015

(65) Prior Publication Data
US 2016/0376441 A1 Dec. 29, 2016

Related U.S. Application Data

(60) Provisional application No. 61/909,602, filed on Nov. 27, 2013.

(30) Foreign Application Priority Data

Nov. 27, 2013 (EP) .................................... 13194728

(51) Int. Cl.
| C07D 491/22 | (2006.01) |
| C09B 11/24 | (2006.01) |
| G01N 33/84 | (2006.01) |
| G01N 31/22 | (2006.01) |

(52) U.S. Cl.
CPC ............ *C07D 491/22* (2013.01); *C09B 11/24* (2013.01); *G01N 31/22* (2013.01); *G01N 33/84* (2013.01)

(58) Field of Classification Search
CPC ....... C07D 491/22; G01N 33/84; C09B 11/24
See application file for complete search history.

(56) References Cited

U.S. PATENT DOCUMENTS 7,102,005 B2 * 9/2006 Agnew .................. G01N 33/50
544/287
2005/0233467 A1 10/2005 Minta et al.

FOREIGN PATENT DOCUMENTS

| EP | 0286402 | 10/1988 |
| EP | 0314480 | 5/1989 |
| WO | 2008/151303 | 12/2008 |

OTHER PUBLICATIONS

Collot et al, "Calcium Rubies: a family of red-emitting functionalizable indicators suitable for two-photon Ca2+ imaging", JACS, vol. 134, Jul. 2012, pp. 14923-14931.
Gaillard et al., "Synthesis and characterization of a new red-emitting Ca2+ indicator, calcium ruby", Organic Letters, vol. 9, No. 14, Jun. 2007, pp. 2629-2632.
Kao et al., "Photochemically Generated Cytosolic Calcium Pulses and Their Detection by Fluo-3", The Journal of Biological Chemistry, vol. 264, No. 14, May 15, 1989, pp. 8179-8184.
Thomas et al., "A comparison of fluorescent Ca2+ indicator properties and their use in measuring elementary and global Ca2+ signals", Cell Calcium, vol. 28, No. 4, Aug. 2000, pp. 213-223.
Tsien, "New Calcium Indicators and Buffers with High Selectivity against Magnesium and Protons: Design, Synthesis, and Properties of Prototype Structures", Biochemistry, vol. 19, No. 11, 1980, pp. 2396-2404.
Zhao et al., "An Expanded Palette of Genetically Encoded Ca2+ Indicators", Science, vol. 333, Sep. 30, 2011, pp. 1888-1891.

* cited by examiner

*Primary Examiner* — Joseph Kosack
(74) *Attorney, Agent, or Firm* — Young & Thompson

(57) ABSTRACT

Compounds of formula I and a process for manufacturing the compounds. A method of using the compounds for the detection of calcium ions and a method of detecting intracellular calcium are also described.

10 Claims, 10 Drawing Sheets

FLUORESCENT RED EMITTING FUNCTIONALIZABLE CALCIUM INDICATORS

FIELD OF INVENTION

The present invention relates to calcium indicators and use thereof for calcium detection, especially fluorescent red-emitting functionalizable calcium indicators. The invention further relates to a process for manufacturing said calcium indicators.

BACKGROUND OF INVENTION

Fluorescent $Ca^{2+}$ indicators are indispensable tools for studying spatiotemporal fluctuations of intracellular free $Ca^{2+}$ concentration ($[Ca^{2+}]_i$). $Ca^{2+}$ is an ubiquitous second messenger involved in numerous intracellular signaling cascades. Biological $Ca^{2+}$ signals gain their specificity from operating at different temporal, spatial, and concentration scales. Temporally, $Ca^{2+}$ transients cover the submillisecond to hour scale. Confined transients microdomains coexist with large-scale fluctuations which propagate through multicellular networks that extend over hundreds of micrometers. Cellular transients signals cover concentrations from near ~100 nM for the basal free $[Ca^{2+}]_i$ of most mammalian cells to >100 μM at the peak of $Ca^{2+}$ microdomains. Thus, depending on the specific $Ca^{2+}$ signal investigated, $Ca^{2+}$ indicators with different affinity for $Ca^{2+}$ binding ($K_{D,Ca}$) are required as fluorescent reporters.

Calcium indicators are used for imaging in neurosciences, in virology, in cardiology.

The fast on-rate for $Ca^{2+}$ binding and high selectivity for $Ca^{2+}$ over $Mg^{2+}$ has made from BAPTA (1,2-bis(o-aminophenoxy)ethane-N,N,N',N'-tetraacetic acid) the most popular $Ca^{2+}$ chelator used in the synthesis of chemical $Ca^{2+}$ indicators (Tsien, R. Y., *Biochemistry*, 1980, 19, 2396). A broad range of indicators has been synthesized by linking or integrating BAPTA to various fluorophores.

Upon binding of $Ca^{2+}$ in the chelating moiety BAPTA, the optical properties of the fluorophore are affected in a detectable way and this change may be correlated with the presence of $Ca^{2+}$ according to a defined standard. This is based on the "PET effect" (Photoinduced Electron Transfert) from the BAPTA ionophoric moiety to the fluorophore moiety, which leads to a decrease in the relative fluorescence intensity and the fluorescence decay time of the fluorophore. By the binding of $Ca^{2+}$ to BAPTA, the PET effect may be partly or totally inhibited, so that there is an increase in the fluorescence of the fluorophore moiety. Hence the concentration of $Ca^{2+}$ can be deduced by measuring the change in fluorescence properties, i.e. fluorescence intensity and/or fluorescence decay time.

Most $Ca^{2+}$ indicators combine BAPTA with fluorescein derivatives and hence emit yellow/green fluorescence (Kao et al., *J. Biol. Chem.*, 1989, 264, 8179; Thomas et al., *Cell Calcium*, 2000, 28, 213). However, the increasing use of cells transfected with fluorescent proteins (FPs), especially eGFP (enhanced Green Fluorescent Protein), of FP-expressing transgenic mice for targeting identified subpopulations of cells, together with the advent of optical techniques for purposes other than imaging, require the development of new genetically encoded and chemical $Ca^{2+}$ probes.

Green or yellow FP tags are the most common chromophores used for $Ca^{2+}$ indicators. GECO-R is the sole red-emitting genetically encoded $Ca^{2\pm}$-sensor (Zhao et al, *Science's STKE*, 2011, 333, 1888) whereas other FP-based $Ca^{2+}$ indicators remain limited to green. The demand for longer-wavelength and higher signal-to-noise chemical $Ca^{2+}$ indicators is accentuated by the recent trend toward all-optical manipulation and recording. Photopharmacology, photochemical uncaging, and optogenetics all use near-ultraviolet or short visible wavelengths that further restrain the part of the visible spectrum available for $Ca^{2+}$ imaging.

Taken together, to be valuable for biological $Ca^{2+}$ imaging, new $Ca^{2+}$ probes should be bright, operate in spectral windows outside the yellow/green, and have a tunable $K_{D,Ca}$.

The main reason for the dominance of fluorescein as fluorophore is its very favorable photo-physical properties (high absorptivity, large quantum yield, and an excitation maximum close to the 488 nm laser line). The X-Rhodamine chromophore is similarly bright as fluorescein, but is red-shifted in both excitation (574 nm) and emission (600 nm) (it is not pH sensitive in the biological pH range and is photostable) and thus presents a suitable alternative fluorophores for indicator design.

Calcium indicators based on rhodamine as fluorophore and BAPTA as $Ca^{2+}$ chelate are for example described in patent EP0 314 480, enabling to work at long wavelengths. Even if affinity for $Ca^{2+}$ is interesting, ranging from 370 nM to 2.3 μM, these indicators present the drawback to have a low quantum yield, i.e. a small or negligible shift to absorbance, excitation or emission wavelengths upon $Ca^{2+}$ binding.

The Applicant described a first family of red emitting calcium indicators based on X-Rhodamine as fluorophore and BAPTA as $Ca^{2+}$ chelate (Scheme 1): Calcium Rubies (CaRubies) (Gaillard et al., Org. Lett., 2007, 9(14), 2629-2632; Collot, M. et al. JACS, 2012, 134, 14923-14931), which had the additional feature of bearing an azido side arm suitable for functionalization by click chemistry (Kolb, H. C. et al. *Angew Chem Int Edit* 2001, 40, 2004).

Scheme 1. Calcium Rubies and associated affinity for $Ca^{2+}$ binding

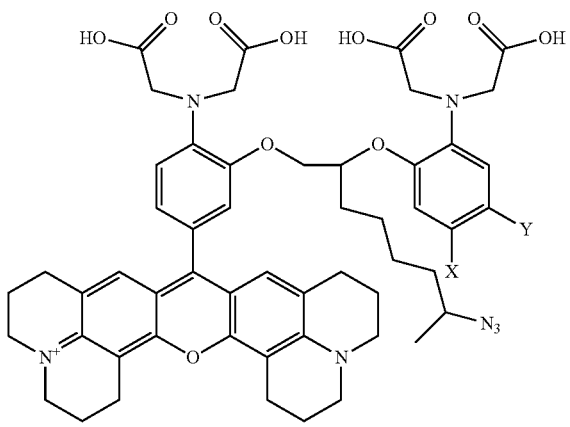

X = H,  Y = Cl  Kd = 21.6 μM
X = F,  Y = H   Kd = 6.2 μM
X = Me, Y = H   Kd = 3.4 μM

Although CaRubies exhibit good spectral properties, two-photon imaging capabilities and multicolor imaging using optogenetics, their dissociation constants ranged from 3.4 to 21.6 μM which was not ideal for the detection of small $[Ca^{2+}]$ transients in biological tissue.

There is therefore a need for new bright red emitting $Ca^{2+}$ indicators having a tunable affinity for calcium ranging from the submicromolar range to micromolar range. Especially, there is a need for a series of calcium indicators having increasing affinities, the more sensible calcium indicator of the series having an affinity of less than 300 nM.

The present invention relates to new red emitting $Ca^{2+}$ indicators comprising a rhodamine moiety and a chelating moiety derived from BAPTA. Especially, the invention relates to a compound of formula I

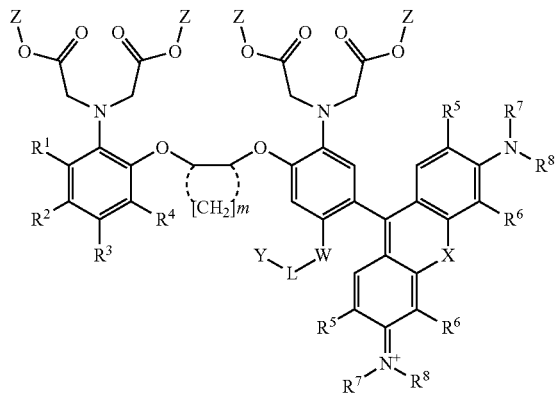

wherein Z, $R^1$, $R^2$, $R^3$, $R^4$, m, W, L, Y, $R^5$, $R^6$, $R^7$, $R^8$ and X are as defined below.

Depending on the substituents of the red-emitting $Ca^{2+}$ indicators of the invention, affinity for calcium ranging may be modulated. Advantageously, the red-emitting $Ca^{2+}$ indicators of the invention have a tunable affinity for calcium ranging from the submicromolar range to micromolar range.

It is noteworthy that the fluorophore (rhodamine derivative) is placed in meta position to the nitrogen of the BAPTA, whereas it is in para in every $Ca^{2+}$ indicators disclosed in the prior art. This shift from para to meta position was surprisingly shown enabling to obtain higher affinities for $Ca^{2+}$ while keeping optical properties of the fluorophore and without modifying the efficacy of PET quenching.

Using two-photon microscopy and simultaneous patch-clamp recording, it was evidenced that the red emitting $Ca^{2+}$ indicators of the invention give signals comparable to commonly used green emitting $[Ca^{2+}]$ probes.

Using high-speed random access microscopy, the Applicant further showed that the red emitting $Ca^{2+}$ indicators of the invention report $[Ca^{2+}]$ transients with kinetics comparable to commonly used indicators.

In vivo patch-clamp recordings demonstrated that the red emitting $Ca^{2+}$ indicators of the invention are $Ca^{2+}$ indicators well suited for a wide range of neuroscience experiments, with a signal quality comparable to previously used high-affinity green emitting probes.

Using the strongly overlapping two-photon excitation spectra of eGFP and of the $Ca^{2+}$ indicator of the invention, a set of experiments was conducted, which was previously not possible. Especially, the potential of two-channel functional imaging was demonstrated with the red emission and high sensitivity of the indicator of the invention being an ideal match for numerous other indicators emitting in the green-yellow spectral band.

It was also evidenced that dual color imaging is also possible and efficient in vivo with the red emitting $Ca^{2+}$ indicator of the invention in the presence of eYFP.

As a consequence, the red emitting $Ca^{2+}$ indicators of the invention are ideal indicators for small intracellular $[Ca^{2+}]$ transients. It was shown that the red emitting calcium indicators of the invention are ideal for both in vitro and in vivo imaging experiments requiring high sensitivity to $[Ca^{2+}]$ changes.

Moreover, the $Ca^{2+}$ indicators of the invention may be combined with activity indicators emitting in the green-yellow spectral band, to allow multiplexed imaging.

Furthermore, the versatility of the indicators of the invention is further increased since they may be functionalized with numerous molecular tools such as for example an antibody, a benzylguanine (SNAP tag) or a peptide to facilitate specific sub-cellular targeting. Especially, the presence of the functionalizable arm enables to introduce moieties suitable to control the localization of the indicator, to make it enter into the cell and to avoid its accumulation in mitochondria once entered in to the cell. Penetrating forms comprising an ester (such as for example an acetoxymethyl—AM) or a dextran are particularly advantageous. With a dextran functionalization, the indicator remains in the cytoplasm.

Indicators of the invention present the advantage that affinity for $Ca^{2+}$ is not modified upon functionalization.

The red emitting calcium indicators of the invention further present the advantage to be specific to their intended function and not affected by other biologically important metal ions, such as for example $Mg^{2+}$, $Na^+$ and $K^+$.

Therefore, the red emitting calcium indicators of the invention are powerful and versatile indicators with tunable calcium affinities.

DEFINITIONS

In the present invention, the following terms have the following meanings:

"about" preceding a figure, means plus or less 10% of the value of said figure.

"rhodamine" refers to a family of related chemical compounds which are heterotricyclic and fluorescent and based on fluorone. Rhodamine refers for example to Rhodamine 6G, Rhodamine B, X-rhodamine.

"fluorophore" refers to a molecule or a portion of molecule which exhibits fluorescence.

"alkyl" refers to a hydrocarbyl radical of formula $C_nH_{2n+1}$ wherein n is a number greater than or equal to 1. Generally, alkyl groups of this invention comprise from 1 to 12 carbon atoms, preferably from 1 to 6 carbon atoms. Alkyl groups may be linear or branched and may be substituted as indicated herein. Suitable alkyl groups include methyl, ethyl, propyl (n-propyl, i-propyl, n-butyl), butyl (i-butyl, s-butyl and t-butyl), pentyl and its isomers (e.g. n-pentyl, iso-pentyl), and hexyl and its isomers (e.g. n-hexyl, iso-hexyl).

"aryl" refers to a polyunsaturated, aromatic hydrocarbyl group having a single ring (i.e. phenyl) or multiple aromatic rings fused together (e.g. naphtyl) or linked covalently, typically containing 5 to 20 atoms; preferably 6 to 12, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl group, the biphenyl group, the 1-naphthyl group, the 2-naphthyl group, the tetrahydronaphthyl group, the indanyl group and the binaphthyl group.

"alkyne" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkyl groups. Non limiting examples of alkynyl groups are ethynyl, 2-propynyl, 2-butynyl, 3-butynyl, 2-pentynyl and its isomers, 2-hexynyl and its isomers- and the like.

"amino" refer to the group —$NH_2$. "alkylamino" refers to the group —NHR wherein R is alkyl. "dialkylamino" refers to the group —NRR' wherein R and R' are alkyl.

"aminocarbonyl" refer to the group —C(O)NR'R" wherein R' and R" are independently selected from the group comprising hydrogen, alkyl, alkenyl, alkynyl, aryl, cycloalkyl, cycloalkenyl, heteroaryl and heterocyclic, and wherein R' and R" are optionally joined together with the nitrogen bound thereto to form a heterocyclic or substituted heterocyclic group, such as for example a substituted piperazine.

"aminothiocarbonyl" refer to the group —C(S)NR'R" wherein R' and R" are independently selected from the group comprising hydrogen, alkyl, alkenyl, alkynyl, aryl, cycloalkyl, cycloalkenyl, heteroaryl and heterocyclic, and wherein R' and R" are optionally joined together with the nitrogen bound thereto to form a heterocyclic or substituted heterocyclic group, such as for example a substituted piperazine.

"halo" means fluoro, chloro, bromo, or iodo. Preferred halo groups are fluoro and chloro.

"dextran" refers to a complex, branched glucan (i.e. a polysaccharide made of many glucose molecules) composed of chains of varying lengths. The straight chain consist of α-1,6 glycosidic linkages between glucose molecules, while branches begin from α-1,3 linkages.

"AM ester" or "AM" as used therein, by itself or as part of another group, refers to an acetoxymethyl ester.

"salt" of the compounds of the invention include the acid addition and base salts thereof. Suitable acid addition salts are formed from acids which form non-toxic salts. Non-limiting examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Non-limiting examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

"fatty acid" refers to a carboxylic acid with a long aliphatic chain, which is either saturated or unsaturated. Preferably the aliphatic chain has a number of carbon atoms ranging from 4 to 28. In a preferred embodiment, fatty acids are derived from triglycerides or phospholipids.

"linker" refers to a single covalent bond or a moiety comprising series of stable covalent bonds, the moiety often incorporating 1-40 plural valent atoms selected from the group consisting of C, N, O, S and P, that covalently attach a reactive group or bioactive group to the calcium probe of the invention. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups (or both). Examples of such pendant moieties are hydrophilicity modifiers, for example solubilising groups like, e.g. sulfo (—$SO_3H$ or —$SO_3^-$).

In one embodiment, L is composed of any combination of single, double, triple or aromatic carbon-carbon bonds, carbon-nitrogen bonds, nitrogen-nitrogen bonds, carbon-oxygen bonds and carbon-sulfur bonds. Linkers may by way of example consist of a combination of moieties selected from alkyl, —C(O)NH—, —C(O)O—, —NH—, —S—, —O— —C(O)—, —S(O)$_n$— where n is 0, 1 or 2; —O—, 5- or 6-membered monocyclic rings and optional pendant functional groups, for example sulfo, hydroxy and carboxy.

The reactive group may be reacted with a substance reactive therewith, whereby the linker becomes bonded to a bioactive group. In this case, the linker typically contains a residue of a reactive group (such as for example the carbonyl group of an ester or a triazolo group resulting from a click reaction between an azide and an alkyne). By "triazolo group" it is referred to the following moiety:

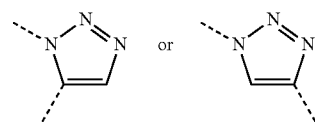

"reactive group" refer to a group capable of reacting with another chemical group to form a covalent bond, i.e. is covalently reactive under suitable reaction conditions, and generally represents a point of attachment for another substance. The reactive group is a moiety on the compounds of the present invention that is capable of chemically reacting with a functional group on a different compound to form a covalent linkage. Reactive groups generally include nucleophiles, electrophiles and photoactivable groups.

DETAILED DESCRIPTION

Compounds

The present invention relates to a calcium indicator comprising a red-emitting probe and a $Ca^{2+}$ probe, as schematically represented on FIG. 1.

In a preferred embodiment, the present invention relates to a calcium indicator comprising a rhodamine moiety and a $Ca^{2+}$ chelating moiety derived from BAPTA. Especially, the invention relates to a compound of formula I

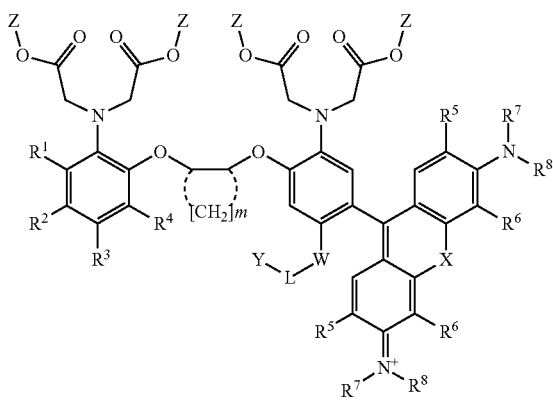

and salts thereof, wherein

Z represents H, alkyl, $CH_2$—OAc, $Na^+$, $K^+$;

$R^1$, $R^2$, $R^3$ and $R^4$ represent each independently H, halo, alkyl, $COR^{11}$, $OR^{11}$, $SR^{11}$, $NR^{11}R^{12}$, wherein $R^{11}$ and $R^{12}$ represent each independently H, alkyl, aryl;

m represents 0, 3 or 4;

W represents O, $NR^9$, S or $CR^9R^{10}$, wherein $R^9$ and $R^{10}$ represent each independently H, alkyl;

L represents a single bound or a linker selected from the group comprising alkyl, aryl, alkylaryl, arylalkyl, polyethylene glycol (PEG), polypropylene glycol (PPG), peptide, aminocarbonyl, alkylaminocarbonyl, aminothiocarbonyl or a combination thereof; optionally additionally comprising a residue of a reactive group through which L is bounded to Y;

Y represents
a reactive function selected from the group comprising $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines;

a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polymeric microparticle, nanoparticle, fluorophore, chromophore, radioisotope, macrocyclic complexes of radioisotope, and combinations thereof;

$R^5$ and $R^6$ each independently represent H, alkyl, halo; $R^7$ and $R^8$ each independently represent H, alkyl; or $R^5$ and $R^7$ are linked together in a single alkyl moiety, preferably propyl, to form a ring with adjacent carbon and nitrogen atoms; or $R^6$ and $R^8$ are linked together in a single alkyl moiety, preferably propyl, to form a ring with adjacent carbon and nitrogen atoms;

X represents O, $NR^9$, S, $CR^9R^{10}$, Se, Si, wherein $R^9$ and $R^{10}$ represent each independently H, alkyl.

According to one embodiment, the invention relates to a compound of formula I or salts thereof wherein Z represents H, alkyl, $CH_2$—OAc, $Na^+$, $K^+$;

$R^1$, $R^2$, $R^3$ and $R^4$ represent each independently H, halo, alkyl, $COR^{11}$, $OR^{11}$, $SR^{11}$, $NR^{11}R^{12}$, wherein $R^{11}$ and $R^{12}$ represent each independently H, alkyl, aryl;

m represents 0, 3 or 4;

W represents O, $NR^9$, S or $CR^9R^{10}$, wherein $R^9$ and $R^{10}$ represent each independently H, alkyl;

L represents a single bound or a linker selected from the group comprising alkyl, aryl, alkylaryl, arylalkyl, polyethylene glycol (PEG), polypropylene glycol (PPG), peptide, aminocarbonyl, alkylaminocarbonyl, aminothiocarbonyl or a combination thereof; optionally additionally comprising a residue of a reactive group through which L is bounded to Y selected from carbonyl group or triazolo group;

Y represents
a reactive function selected from the group comprising $N_3$, amino, alkylamino, COOH, amide, maleimide, alkyne, SH, OH, ester, N-hydroxysuccinimide ester, N-hydroxyglutarimide ester, maleimide ester, acid anhydride, acid halide, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines;

a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, biotin, avidin, synthetic polymer, polymeric microparticle, nanoparticle, fluorophore, chromophore, radioisotope, macrocyclic complexes of radioisotope, and combinations thereof;

$R^5$ and $R^6$ each independently represent H, alkyl, halo; $R^7$ and $R^8$ each independently represent H, alkyl; or $R^5$ and $R^7$ are linked together in a single alkyl moiety, preferably propyl, to form a ring with adjacent carbon and nitrogen atoms; or $R^6$ and $R^8$ are linked together in a single alkyl moiety, preferably propyl, to form a ring with adjacent carbon and nitrogen atoms;

X represents O, $NR^9$, S, $CR^9R^{10}$, Se, Si, wherein $R^9$ and $R^{10}$ represent each independently H, alkyl.

According to one embodiment, when $R^5$ and $R^7$ are linked together in a single alkyl moiety, the single alkyl moiety is propyl. According to one embodiment, when $R^6$ and $R^8$ are linked together in a single alkyl moiety, the single alkyl moiety is propyl.

According to one embodiment, when $R^5$ and $R^7$, or $R^6$ and $R^8$, are linked together in a single alkyl moiety, the single alkyl moiety is propyl.

According to an embodiment, activated ester refers for example to N-hydroxysuccinimide ester, N-hydroxyglutarimide ester or maleimide ester.

According to an embodiment, activated carboxylic acid refers for example to acid anhydride or acid halide.

According to one embodiment, Y represents a reactive function selected from the group comprising $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines.

According to a preferred embodiment, Y represents a reactive function selected from the group comprising $N_3$, alkyne, amino, alkylamino, COOH, amide, maleimide, SH, OH, ester, activated ester, activated carboxylic acid. Preferably, Y represents a reactive function selected from the group comprising $N_3$, alkyne, amino, alkylamino, COOH, amide, maleimide, SH, OH, ester, N-hydroxysuccinimide ester, N-hydroxyglutarimide ester, maleimide ester, acid anhydride, acid halide, According to one embodiment, Y represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polymeric microparticle, nanoparticle, fluorophore, chromophore, radioisotope, macrocyclic complexes of radioisotope, and combinations thereof. Preferably, Y represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, biotin, avidin, synthetic polymer, polymeric microparticle, nanoparticle, fluorophore, chromophore, radioisotope, macrocyclic complexes of radioisotope, and combinations thereof.

According to a preferred embodiment, Y represents a bioactive group selected from amino acid, peptide, protein, antibody, enzyme, polysaccharide, dextran, benzylguanine, lipid, lipid assembly, fatty acid, ligand, substrate, biotin, avidin, fluorophore, chromophore. Preferably, Y represents a bioactive group selected from amino acid, peptide, protein, antibody, enzyme, polysaccharide, dextran, benzylguanine, lipid, lipid assembly, fatty acid, biotin, avidin, fluorophore, chromophore.

The compound of the invention presents the advantage to be functionalizable or functionalized. Functionalization is preferably performed at Y position on the BAPTA chelating moiety.

According to an embodiment, the compound of the invention is of formula Ia

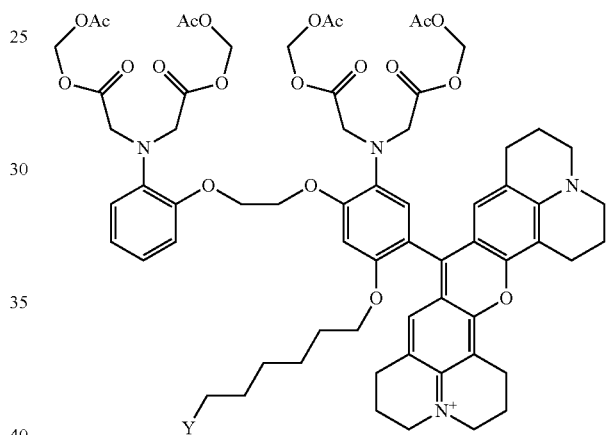

and salts thereof, wherein W, L, Y, $R^5$, $R^6$, $R^7$, $R^8$ and X are as defined in formula I.

According to a specific embodiment, the compound of the invention is of formula Ia-1:

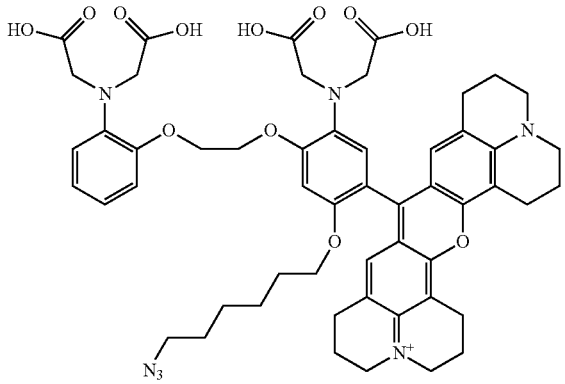 [SMILES: [N-]=[N+]=NCCCCCCOc1cc(OCCOc2ccccc2N(CC(=O)O)CC(=O)O)c(N(CC(=O)O)CC(=O)O)cc1C1=c2cc3c4c(c2Oc2c1cc1c5c2CCCN5CCC1)CCC[N+]=4CCC3]

According to an embodiment, the compound of the invention is of formula Ia-2

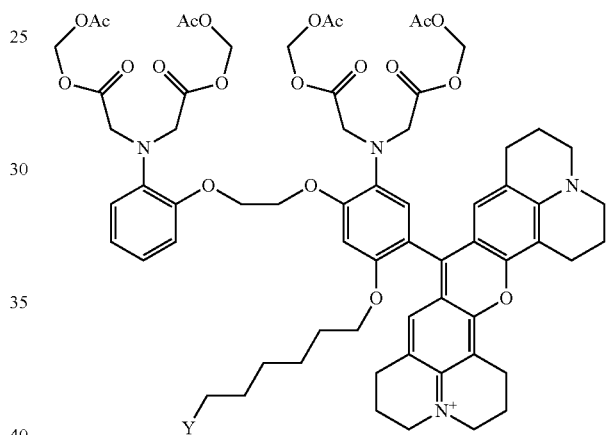

wherein Y represent a dextran bioactive group.

In one embodiment, compound of formula Ia-2 is obtained by a reaction of click chemistry between the azide function of compound of formula Ia-1 and a propargylated dextran triazole ring formation.

According to an embodiment, the compound of the invention is of formula Ib

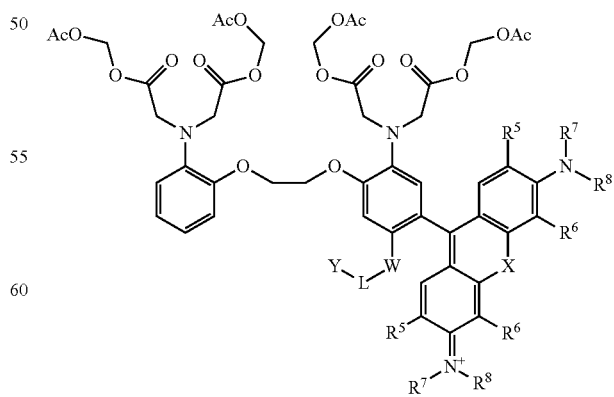

and salts thereof, wherein W, L, Y, $R^5$, $R^6$, $R^7$, $R^8$ and X are as defined in formula I.

According to an embodiment, the compound of the invention is of formula Ib-1

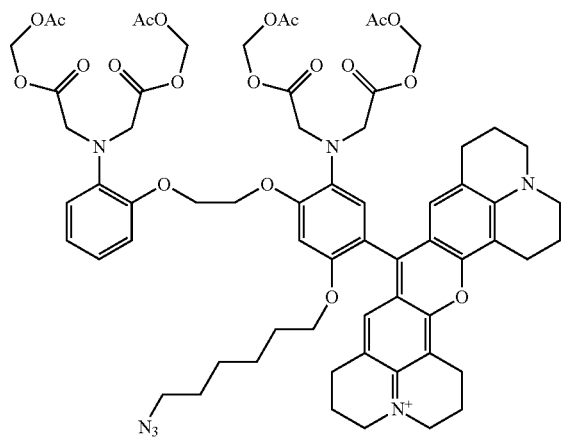 [SMILES: CC(=O)OCOC(=O)CN(CC(=O)OCOC(C)=O)c1ccccc1OCCOc1cc(OCCCCCCN=[N+]=[N-])c(C2=c3cc4c5c(c3Oc3c2cc2c6c3CCCN6CCC2)CCC[N+]=5CCC4)cc1N(CC(=O)OCOC(C)=O)CC(=O)OCOC(C)=O]

According to an embodiment, the compound of the invention is of formula Ic

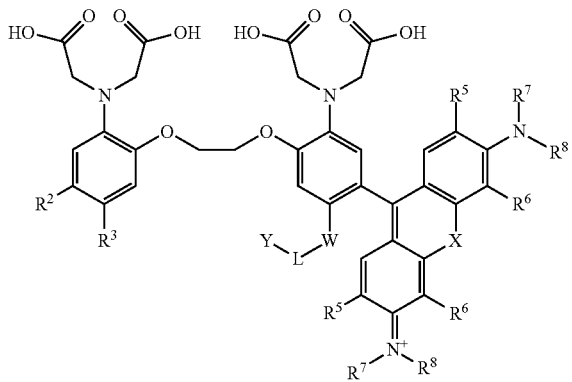

and salts thereof, wherein $R^2$, $R^3$, W, L, Y, $R^5$, $R^6$, $R^7$, $R^8$ and X are as defined in formula I.

According to a specific embodiment, the compound of the invention is of formula Ic-1 or Ic-2:

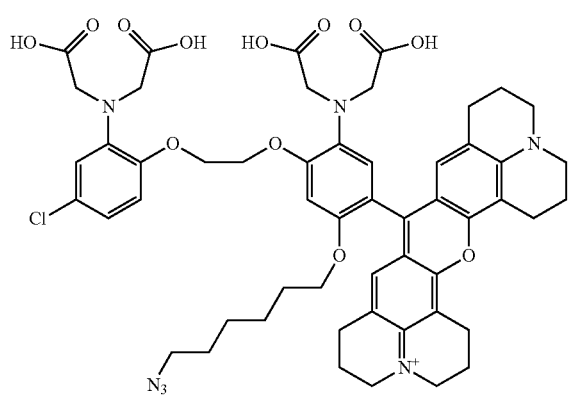

(Ic-1)

(Ic-2)

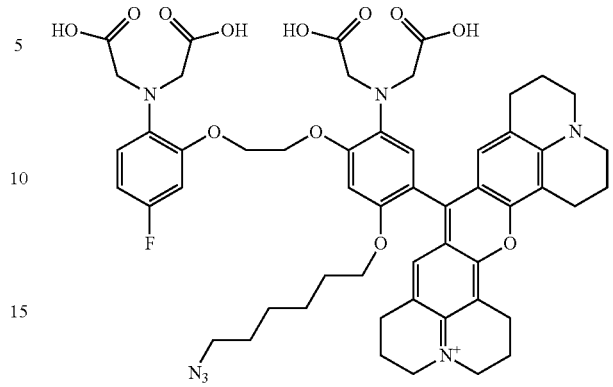

According to one embodiment, the compound of the invention is selected from the group comprising compounds of formula Ia-1, Ia-2, Ib-1, Ic-1 and Ic-2:

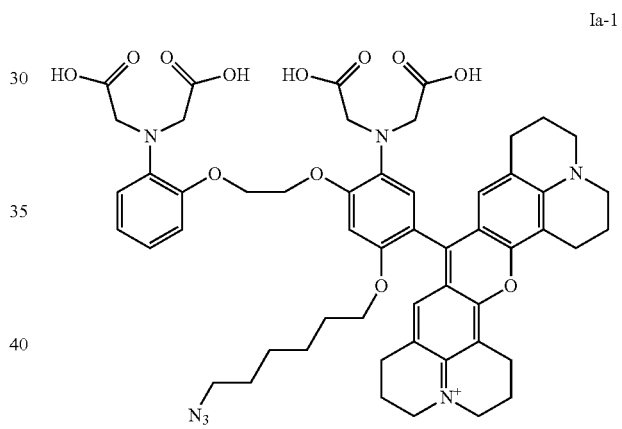

(Ia-1)

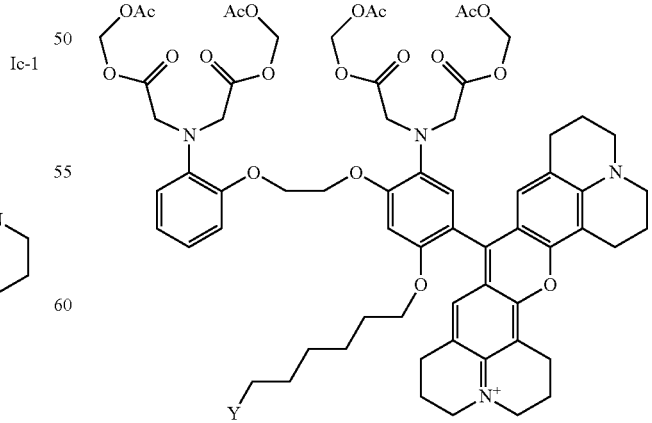

(Ia-2)

wherein Y represent a dextran bioactive group;

-continued

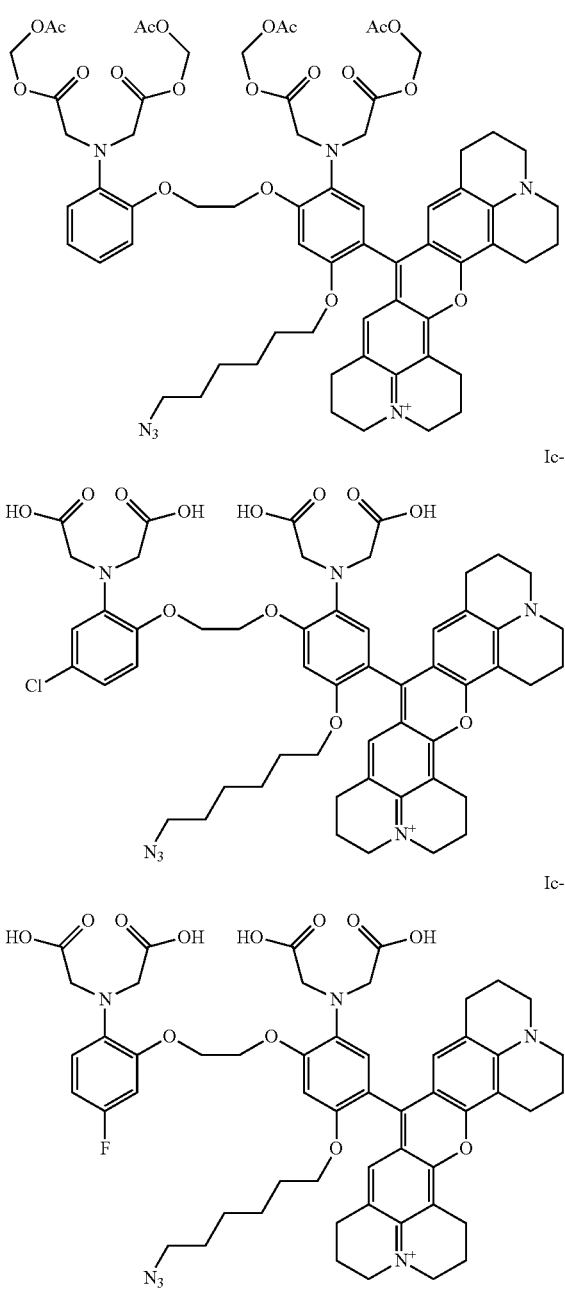

Ib-1

Ic-1

Ic-2

Affinity for Calcium

According to one embodiment, the compound of the invention has an affinity for calcium ranging from 200 nM to 50 μM. Depending on substituents on the chelating moiety, it is advantageously possible to modulate affinity for calcium. In a first embodiment, the compound of the invention has an affinity for calcium ranging from 200 to 400 nM. In a second embodiment, the compound of the invention has an affinity for calcium ranging from 400 to 600 nM. In a third embodiment, the compound of the invention has an affinity for calcium ranging from 600 to 900 nM. In a fourth embodiment, the compound of the invention has an affinity for calcium ranging from 0.9 to 1 μM. In a fifth embodiment, the compound of the invention has an affinity for calcium ranging from 1 to 10 μM. In a sixth embodiment, the compound of the invention has an affinity for calcium ranging from 10 to 50 μM.

Upon functionalization, affinity for calcium of the compound of the invention is not affected.

Fluorescence

According to an embodiment, the compound of the invention is fluorescent. Preferably the compound of the invention is a red fluorescent indicator. According to preferred embodiment, the compound of the invention emits at a wavelength of more than 600 nm.

In an embodiment, the compound of the invention has a quantum yield ranging from 42 to 46%, preferably about 45%. Quantum yield may be measured by as described in "Measurement of Fluorescence Quantum Yields", Michael W. Allen, Thermo Fisher Scientific, Madison, Wis., USA.

In an embodiment, the compound of the invention may be characterized by its dynamic range. Dynamic range may be measured by spectrofluorimetry with solutions of increasing $Ca^{2+}$ concentration.

Process for Manufacturing

The compounds of the invention may be prepared using any suitable reactions known by those skilled in the art.

The invention further relates to a process for manufacturing the compounds of the invention.

In a preferred embodiment, the process of the invention comprises the step represented on the scheme below:

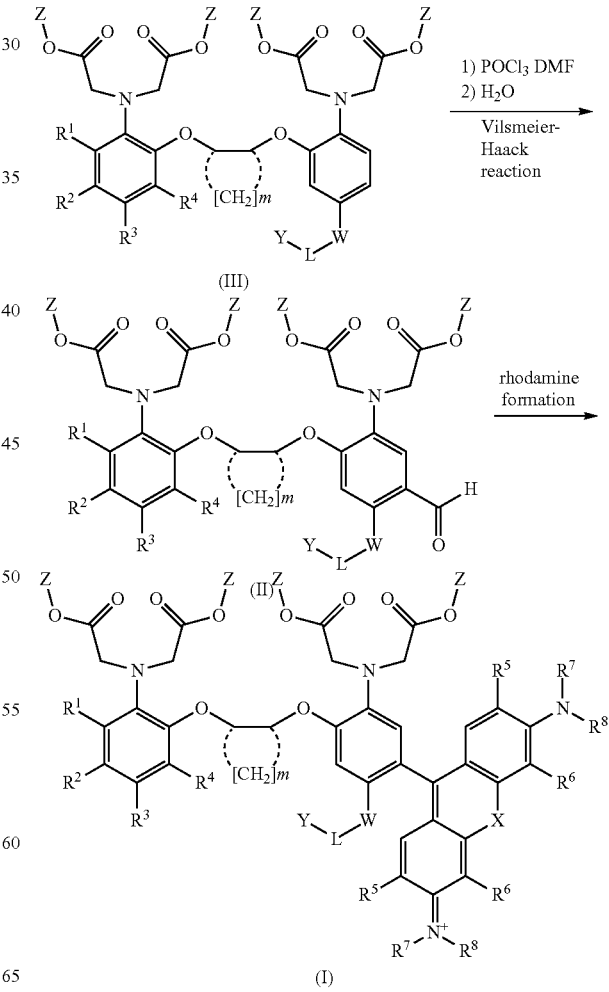

According to one embodiment, the invention relates to a process for manufacturing a compound of formula I as defined above, comprising performing a Vilsmeier-Haack reaction on a compound of formula III

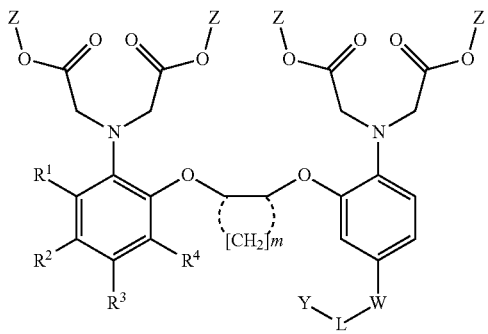

wherein Z, $R^1$, $R^2$, $R^3$, $R^4$, m, W, L and Y are as defined above;

leading to compound of formula II

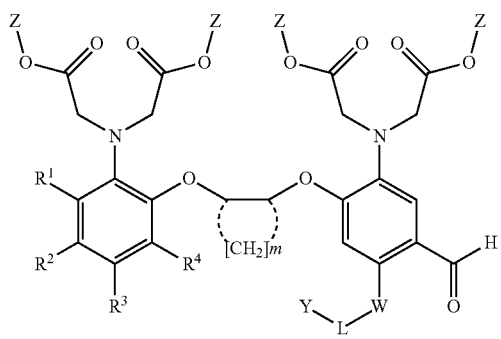

wherein Z, $R^1$, $R^2$, $R^3$, $R^4$, m, W, L and Y are as defined above;

and further comprising a step of rhodamine formation on the aldehyde function of compound of formula II, to afford compound of formula I.

Especially, the invention relates to a process for manufacturing a compound of formula I

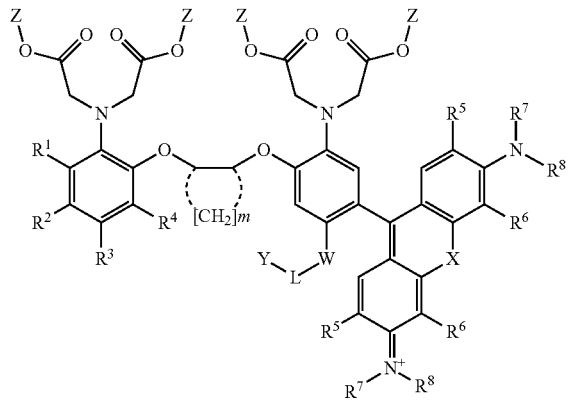

and salts thereof, wherein

Z represents H, alkyl, $CH_2$—OAc, $Na^+$, $K^+$;

$R^1$, $R^2$, $R^3$ and $R^4$ represent each independently H, halo, alkyl, $COR^{11}$, $OR^{11}$, $SR^{11}$, $NR^{11}R^{12}$, wherein $R^{11}$ and $R^{12}$ represent each independently H, alkyl, aryl;

m represents 0, 3 or 4;

W represents O, $NR^9$, S or $CR^9R^{10}$, wherein $R^9$ and $R^{10}$ represent each independently H, alkyl;

L represents a single bound or a linker selected from the group comprising alkyl, aryl, alkylaryl, arylalkyl, polyethylene glycol (PEG), polypropylene glycol (PPG), peptide, aminocarbonyl, alkylaminocarbonyl, aminothiocarbonyl or a combination thereof; optionally additionally comprising a residue of a reactive group through which L is bounded to Y;

Y represents
  a reactive function selected from the group comprising $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines;
  a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polymeric microparticle, nanoparticle, fluorophore, chromophore, radioisotope, macrocyclic complexes of radioisotope, and combinations thereof;

$R^5$ and $R^6$ each independently represent H, alkyl, halo; $R^7$ and $R^8$ each independently represent H, alkyl; or $R^5$ and $R^7$ are linked together in a single alkyl moiety, preferably propyl, to form a ring with adjacent carbon and nitrogen atoms;

or $R^6$ and $R^8$ are linked together in a single alkyl moiety, preferably propyl, to form a ring with adjacent carbon and nitrogen atoms;

X represents O, $NR^9$, S, $CR^9R^{10}$, Se, Si, wherein $R^9$ and $R^{10}$ represent each independently H, alkyl;

comprising performing a Vilsmeier-Haack reaction on a compound of formula III

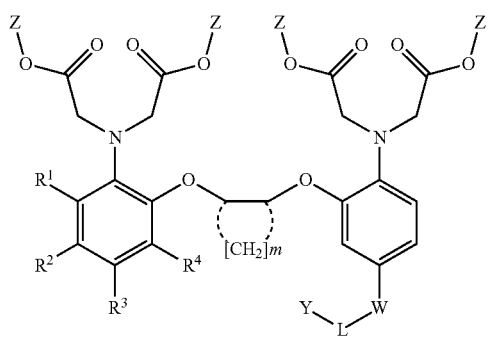

wherein Z, R¹, R², R³, R⁴, m, W, L and Y are as defined above;
leading to compound of formula II

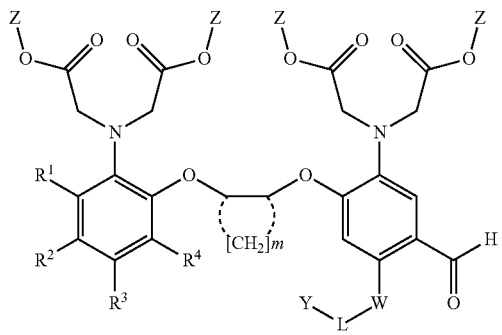

wherein Z, R¹, R², R³, R⁴, m, W, L and Y are as defined above;
and further comprising a step of rhodamine formation on the aldehyde function of compound of formula II, to afford compound of formula I.

According to one embodiment, the process of the invention further comprises one or more subsequent steps selected from:
  modification of Z substituents;
  modification of Y substituent.

In one embodiment, the modification of Y substituent is performed in the case wherein Y is a reactive function (Y'), in order to introduce a bioactive group (Y"). In this embodiment, the step of modification of Y substituent comprises reacting the reactive function Y' with a bioactive group, to link the bioactive group to the compound of the invention, leading to Y'". Consequently, when Y represents a bioactive group, it is implicit that the bioactive group may comprise a linking moiety, such as for example an ester bound, an amide bound or a triazolo group (click chemistry), to be linked to linker L.

According to a preferred embodiment, the Vilsmeier-Haack reaction is performed in presence of dimethylformamide (DMF) and phosphorus oxychloride.

According to one embodiment, the formation of the rhodamine is performed according to methods well-known by those skilled in the art.

According to a preferred embodiment, the aldehyde function of compound of formula II is allowed to react in presence of 8-hydroxyjulolidine and para toluene sulfonic acid and then further in presence of chloranil. According to an embodiment, the aldehyde function of compound of formula II is allowed to react with 2 equivalents of 8-hydroxyjulolidine and a catalytic amount of para toluene sulfonic acid, preferably 0.1 equivalent. Preferably, the reaction is conducted at room temperature. Preferably, the solvent is propionic acid. Preferably the reaction is conducted for a period of time of about 12 hours. According to one embodiment, a solution of chloranil is then added, preferably a solution in dichloromethane. Preferably, 1 equivalent of chloranil is added.

Use of the Compounds

The present invention further relates to the use of the compounds of the invention as calcium indicators, for the detection of calcium ions. Especially, the compounds of the invention are useful for the detection and/or quantification of $Ca^{2+}$ in a sample of interest.

In a preferred embodiment, the $Ca^{2+}$ is measured in extracellular spaces, in vesicles, in vascular tissues, in biological fluids such as blood or urine.

In an embodiment, the present invention relates to a method of detecting intracellular calcium comprising the use of the compounds of the invention.

According to one embodiment, the method of detecting intracellular calcium comprises:
  adding a compound according to the invention to a sample containing at least one cell;
  incubating the sample for a time sufficient for the compound to be loaded into the cell;
  illuminating the sample at an excitating wavelength that generates a fluorescent response from the indicator;
  detecting the fluorescent response.

According to an embodiment, the method of the invention further comprises:
  stimulating the cell;
  monitoring changes in the intensity of the fluorescent response from the indicator; and
  correlating the changes in fluorescence intensity with changes in intracellular calcium levels.

According to one embodiment, cells of potential interest for detecting intracellular calcium include, but are not limited to, primary culture of mammalian cells, cells dissociated from mammalian tissues. Cell types may include white blood cell, hepatocytes, pancreatic beta cells, neurons, smooth muscle cells, intestinal epithelial cells, cardiac myocytes, glial cells, and the like.

The present invention further relates to a kit for performing a calcium assay, comprising a compound according to the invention. The kit of the invention may comprise a compound of the invention either present as a pure compound, in a suitable carrier composition, or dissolved in an appropriate stock solution. The kit may further comprise instructions for the use of the calcium indicator of the invention. The kit may further comprise one or more additional components, such as an additional detection reagent. In one embodiment, the kit of the invention further comprises water free of calcium. In one embodiment, the kit of the invention comprises ethylenediamine tetraacetic acid (EDTA). According to an embodiment, the kit further comprises calibration standards.

According to one embodiment, the indicator of the invention may be present in the kit associated with a surface, such as for example a chip, microplate well, or other solid or semi-solid matrix.

According to an embodiment, the compound of the invention is functionalized with a fluorophore, preferably a blue probe or a green probe. Such a functionalized compound enables bimodal imaging. In an embodiment, the fluorescence of the fluorophore coupled to the compound of the invention does not depend from the amount of $Ca^{2+}$. In this case, ratiometric studies may be conducted using the fluorophore-functionalized compound of the invention.

In an embodiment, the compound of the invention is functionalized with a radioactive Positron Emission Tomography PET-probe, such as for example $^{18}$F, DOTA or NOTA $^{68}$Ga complexes, enabling PET-scan together with calcium imaging. DOTA refers to 1,4,7,10-tetraazacyclododecane-1,4,7,10-tetraacetic acid, and NOTA represents NOTA-1,4,7-triazacyclononane-1,4,7-triacetic acid. Such bimodal probe presents the advantage to enable detection of a calcic anomaly in a tumor.

In a specific embodiment, the calcium indicator of formula I of the invention, when having Y function bearing a $N_3$ at Y function may be co-administered with modified biomacromolecules to operate intracellular click reaction, as suggested by Takei et al. (Takei et al., ChemComm, 2013, 49, 7313-7315). Especially, the compound of the invention may be administered with a bibenzylcyclooctyl-modified biomacromolecule. The click reaction between the azide function and the alkyne moiety of the modified biomacromolecule aims at retaining the $Ca^{2+}$ indicator in the cytosol of tested cells.

EXAMPLES

Figure 1:
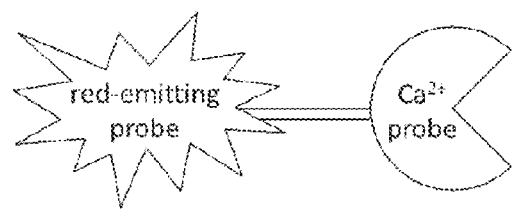
FIG. 1 is a drawing schematically representing the red-emitting calcium indicator of the invention.

The present invention is further illustrated by the following examples.

I. Synthesis

I.1. Materials and General Methods

All the solvents were of analytical grade. Chemicals were purchased from commercial sources. $^1$H-NMR and $^{13}$C-NMR were measured on a Bruker avance 111-300 MHz spectrometer with chemical shifts reported in ppm (TMS as internal standard). Mass spectra were measured on a Focus GC/DSQ II spectrometer (ThermoScientific) for IC and an API 3000 spectrometer (Applied Biosystems, PE Sciex) for ES. All pH measurements were made with a Mettler Toledo pH-Meter. Fluorescence spectra were recorded on a JASCO FP-8300 spectrofluorometer. Absorption spectra were determined on a VARIAN CARY 300 Bio UV-Visible spectrophotometer. All measurements were done at a set temperature of 25° C. The purity of the dyes were checked by RP-HPLC C-18, eluant: ACN 0.1% TFA/Water 0.1% TFA, method: 20/80 to 100/0 within 20 min then 100/0 for 10 min. detection at $\lambda_{Abs}$=254 nm. The apparent dissociation constant for calcium (Kd $Ca^{2+}$) was measured with a calcium calibration buffer kit from Invitrogen.

I.2. Synthesis of Compound Ia-1 and Ib-1
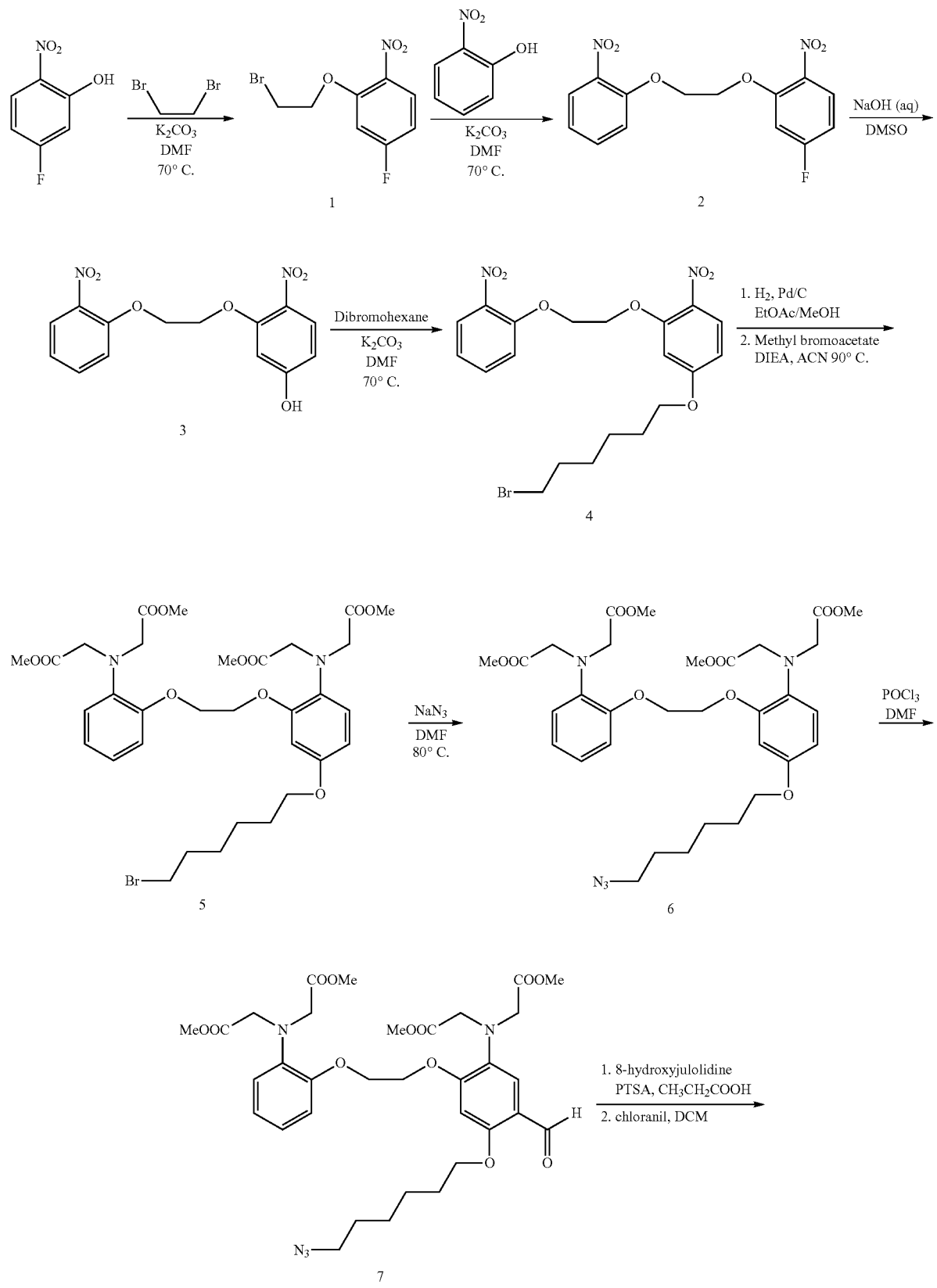
Scheme 2. Synthesis of Ia-1 and Ib-1

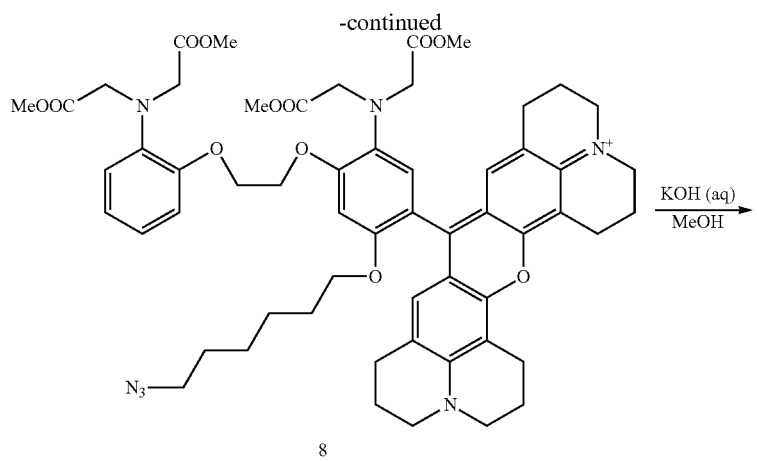
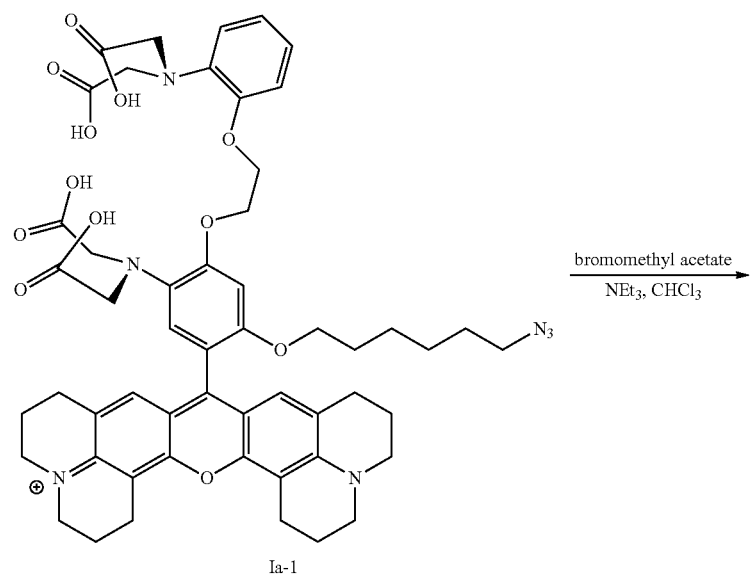
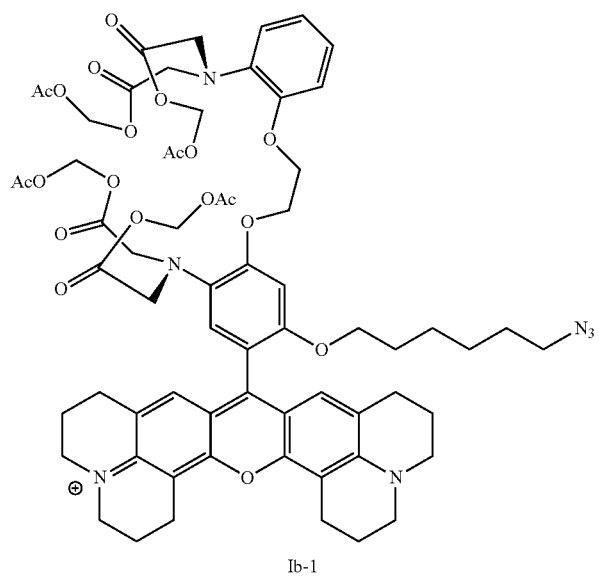

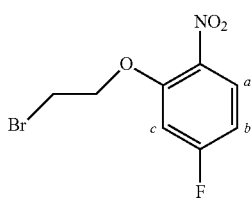

1

To a solution of 5-fluoro-2-nitrophenol (14.90 g, 94.84 mmol) in DMF (75 mL) were added dibromoethane (40.90 mL, 472.2 mmol, 5 eq) and $K_2CO_3$ (26.30 g, 189.7 mmol, 2 eq), the mixture was allowed to stir at 70° C. for 2 h. The solvents were evaporated and the product was extracted with EtOAc, washed with water (3 times) and brine (2 times). The organic phase was dried over $MgSO_4$, filtered and evaporated to reach a volume of 200 mL. The symmetric dinitro compound crystallizes first and was filtered off. The filtrate was then allowed to crystallize to obtain 20.12 g of 1 (80%) as a yellow powder. $^1$H-NMR (300 MHz, DMSO-d6): δ 8.04 (dd, $J_{a\text{-}b}$=9.1 Hz, $J_{a\text{-}F}$=6.1 Hz, 1H, $H_a$), 7.37 (dd, $L_{c\text{-}F}$=11.0 Hz, $J_{c\text{-}b}$=2.6 Hz, 1H, $H_c$), 7.02 (ddd, $J_{b\text{-}a}$=9.1, $J_{b\text{-}F}$=7.8 Hz, $J_{b\text{-}c}$=2.6 Hz, 1H, $H_b$), 4.56-4.53 (m, 2H, $CH_2O$), 3.84-3.81 (m, 2H, $CH_2Br$). $^{13}$C-NMR (75 MHz, DMSO-d6): δ 164.82 (d, $^1J_{F\text{-}C}$=251 Hz, CF), 152.81 (d, $^3J_{C\text{-}F}$=12 Hz, CO), 136.17 (d, $^4J_{F\text{-}C}$=3 Hz, $\underline{C}NO_2$), 127.62 (d, $^3J_{F\text{-}C}$=11 Hz, $C_a$), 108.01 (d, $^2J_{F\text{-}C}$=23 Hz, $C_b$), 103.45 (d, $^2J_{F\text{-}C}$=27 Hz, $C_c$), 69.78 ($\underline{C}H_2O$), 30.39 ($\underline{C}H_2Br$). MS (CI), calcd for $C_8H_{11}BrFN_2O_3$ $[M+NH_4]^+$280.9, found 281.0.

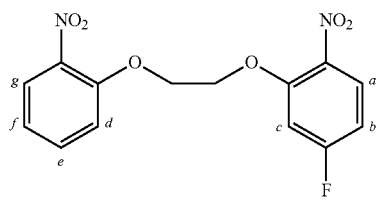

2

To a solution of 1 (19.79 g, 74.96 mmol) in DMF (75 mL) were added 2-nitrophenol (11.46 g, 82.45 mmol, 1.1 eq) and $K_2CO_3$ (15.63 g, 112.4 mmol, 1.5 eq), the mixture was allowed to stir overnight at 70° C. The solvent was evaporated and the product was extracted with DCM, washed with HCl (1M) and brine (2 times). The organic phase was dried over $MgSO_4$, filtered and evaporated to reach a volume of 200 mL. The product crystallized and was filtered to obtain 12.00 g of 2 (50%) as a yellow powder. $^1$H-NMR (300 MHz, DMSO-d6): δ 8.01 (dd, $J_{a\text{-}b}$=9.1 Hz, $J_{a\text{-}F}$=6.1 Hz, 1H, $H_a$), 7.86 (dd, $J_{g\text{-}f}$=8.1 Hz, $J_{g\text{-}e}$=1.6 Hz, 1H, $H_g$), 7.67 (ddd, $^3J$=8.5, 7.4, $^4J_{e\text{-}g}$=1.7 Hz, 1H, $H_e$), 7.45-7.39 (m, 2H, $H_c$, $H_d$), 7.15 (ddd, $^3J$=8.1 Hz, 7.4, $^4J$=1.1 Hz, 1H, $H_f$), 7.01 (ddd $J_{b\text{-}a}$=9.1, $J_{b\text{-}F}$=7.8 Hz, $J_{b\text{-}c}$=2.6 Hz, 1H, $H_b$), 4.59-4.54 (m, 4H, $2CH_2O$). $^{13}$C-NMR (75 MHz, DMSO-d6): δ 164.86 (d, $^1J_{F\text{-}C}$=251 Hz, $\underline{C}F$), 153.34 (d, $^3J_{C\text{-}F}$=11.9 Hz, $\underline{C}O$), 150.82 (Cq Ar), 139.74 (Cq Ar), 136.15 (d, $^4J_{F\text{-}C}$=3.7 Hz, $\underline{C}NO_2$), 134.33 ($C_e$), 127.58 (d, $^3J_{F\text{-}C}$=11 Hz, $C_a$), 124.85 ($C_g$), 121.05 ($C_f$), 115.55 ($C_d$), 107.90 (d, $^2J_{F\text{-}C}$=24 Hz, $C_b$), 103.57 (d, $^2J_{F\text{-}C}$=27 Hz, $C_c$), 68.57 ($CH_2O$), 67.93 ($CH_2O$). MS (ES+), calcd for $C_{14}H_{11}FN_2O_6Na$ $[M+Na]^+$ 345.0, found 345.3. HRMS (ES+), calcd for $C_{14}H_{11}FN_2O_6Na$ $[M+Na]^+$ 345.0493, found 345.0501.

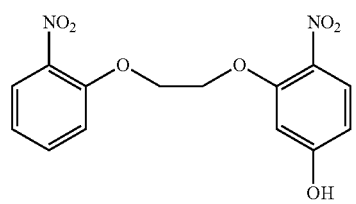

3

To a stirred solution of 2 (5.91 g, 18.34 mmol) in DMSO (53 mL) was added NaOH 20% (11.5 mL) the solution turned yellow and was allowed to stir at room temperature overnight. 50 mL of water and 10 mL HCl (1M) were then added and the product was extracted 3 times with EtOAc. The organic phase was washed 3 times with water before being dried over $MgSO_4$, the solution was filtered and evaporated and crystallized in EtOAc to obtain 4.46 g of 3 (76%) as a yellow powder. $^1$H-NMR (300 MHz, DMSO-d6): δ 7.90-7.85 (m, 2H, $H_a$, $H_g$), 7.67-7.64 (dd, $^3J$=8.7 Hz, $^4J$=1.5 Hz, 1H, $H_e$), 7.48 (d, $^3J$=8.4 Hz, 1H, $H_d$), 7.16 (t, $^3J$=7.7 Hz, 1H, $H_f$), 6.66 (d, $^4J$=2.2 Hz, 1H, $H_e$), 6.51 (dd, $^3J$=9.0, $^4J$=2.2 Hz, 1H, $H_b$), 4.55-4.54 (m, 2H, $CH_2O$), 4.45 (t, J=3.8 Hz, 2H, $CH_2O$). $^{13}$C-NMR (75 MHz, DMSO-d6): δ 163.87 (Cq Ar), 154.51 (Cq Ar), 150.98 (Cq Ar), 139.79 (Cq Ar), 134.36 ($C_e$), 131.12 (Cq Ar), 128.18 ($C_a$ or $C_g$), 124.86 ($C_a$ or $C_g$), 121.03 ($C_f$), 115.75 ($C_d$), 108.01 ($C_b$), 101.56 ($C_c$), 68.06 ($CH_2O$), 67.87 ($CH_2O$). MS (CI), calcd for $C_{14}H_{16}N_3O_7$ $[M+NH_4]^+$338.0, found 337.7. HRMS (ES+), calcd for $C_{14}H_{13}N_2O_7[M+H]^+$ 321.0717, found 321.0722.

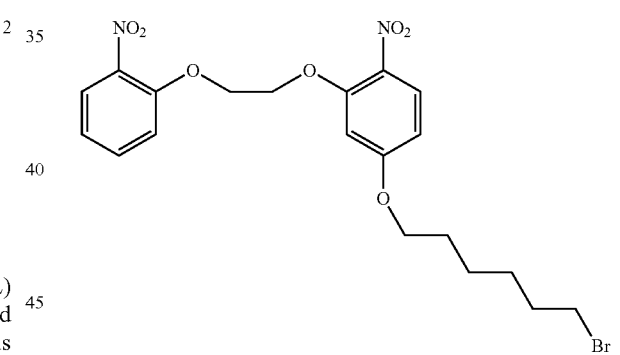

4

To a solution of 3 (4.86 g, 15.19 mmol) in DMF (50 mL) were added dibromohexane (11.12 mL, 45.56 mmol, 3 eq) and $K_2CO_3$ (3.16 g, 22.78 mmol, 1.5 eq). The mixture was allowed to stir at 70° C. for 12 h. The solvents were evaporated and the product was extracted with EtOAc washed with water (3 times) and brine (2 times). The organic phase was dried over $MgSO_4$, filtered and evaporated. The crude was purified by column chromatography on silica gel (Cyclohexane/EtOAc: 7/3) to obtain the crude 4 which was crystallized in a mixture of EtOAc and cyclohexane (3/7) to obtain 2.97 g of pure 4 (40%) as a off white powder. Rf=0.22 (Cyclohexane/EtOAc, 7/3). $^1$H-NMR (300 MHz, $CDCl_3$): δ 8.00 (d, J=9.1 Hz, 1H, $H_a$), 7.86 (dd, J=8.1, 1.6 Hz, 1H, $H_g$), 7.64-7.58 (m, 1H, $H_e$), 7.33 (dd (in solvent peak), 1H, $H_d$), 7.14-7.09 (m, 1H, $H_f$), 6.66 (d, J=2.4 Hz, 1H, $H_c$), 6.57 (dd, J=9.1, 2.4 Hz, 1H, $H_b$), 4.60-4.51 (m, 4H, $2CH_2O$), 4.08 (t, J=6.4 Hz, 2H, $CH_2O$), 3.47 (t, J=6.7 Hz, 2H, $CH_2Br$), 1.96-1.85 (m, 4H, $2CH_2$), 1.56 (dt, J=7.1, 3.5 Hz, 4H, $2CH_2$). $^{13}$C-NMR (75 MHz, $CDCl_3$): δ 164.35 (Cq), 154.63 (Cq), 151.96 (Cq), 140.43 (Cq), 134.37 ($C_e$), 133.34 (Cq), 128.32 ($C_a$), 125.56 ($C_g$), 121.43 ($C_f$), 116.14 ($C_d$), 106.89 ($C_e$), 102.02 ($C_c$), 68.83 ($\underline{CH_2}O$), 68.70 ($\underline{CH_2}O$), 68.65 ($\underline{CH_2}O$), 33.81 ($\underline{CH_2}Br$), 32.63 ($CH_2$), 28.85 ($CH_2$), 27.86 ($CH_2$), 25.19 ($CH_2$). MS (ES+), calcd for $C_{20}H_{23}BrN_2O_7Na$ [M+Na]$^+$ 505.0, found 505.5. HRMS (ES+), calcd for $C_{20}H_{24}BrN_2O_7$ [M+H]$^+$ 483.0767, found 483.0772.

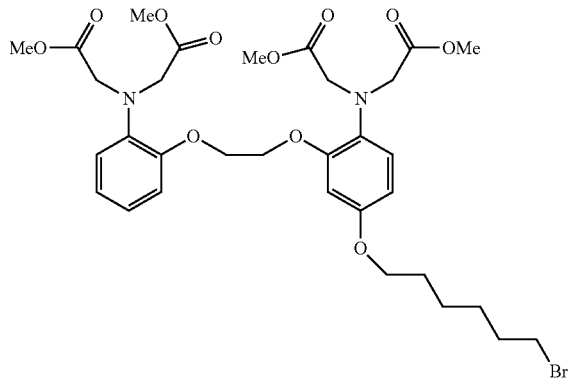

5

To a solution of 4 (5.00 g, 10.35 mmol) in EtOAc (100 mL) and methanol (30 mL) was added Pd/C (1.10 g). The solution was stirred and degassed before $H_2$ was allowed to bubble in the solution for 5 h. The solution was then filtered off celite and rinsed with EtOAc under an atmosphere of argon. The solvents were evaporated and the residue was dissolved in acetonitrile (50 mL), to this solution were added, methyl bromoacetate (12.0 mL, 124.2 mmol, 12 eq) and DIEA (23.0 mL, 124.2 mmol, 12 eq) before being warmed up to 80° C. The solution was allowed to stir overnight at 80° C. The solvents were evaporated, the product was extracted with dichloromethane (DCM) and the organic layer washed with water, was dried over MgSO$_4$, filtered and evaporated. The crude was purified by column chromatography on silica gel (Cyclohexane/EtOAc: 7/3) to give 3.71 g of 5 (50%) as a yellowish syrup containing some impurities (visible between 2 and 3 ppm in $^1$H NMR) that could not be removed at this stage. Rf=0.51 (Cyclohexane/EtOAc, 6/4). $^1$H-NMR (300 MHz, CDCl$_3$): δ 6.85-6.74 (m, 5H), 6.39 (d, J=2.7 Hz, 1H), 6.31 (dd, J=8.7, 2.7 Hz, 1H), 4.20 (m, 4H, $\underline{CH_2}O$), 4.08 (s, 4H, 2$\underline{CH_2}N$), 4.02 (s, 4H, 2 $\underline{CH_2}N$), 3.81 (t, J=6.4 Hz, 2H, $\underline{CH_2}O$), 3.50 (d, J=7.4 Hz, 12H, 4 OMe), 3.36 (t, J=6.8 Hz, 2H, $\underline{CH_2}Br$), 1.85-1.80 (m, 2H, $CH_2$), 1.71-1.67 (m, 2H, $CH_2$), 1.42 (t, J=3.6 Hz, 4H, 2 $CH_2$). MS (ES+), calcd for $C_{32}H_{43}BrN_2O_{11}Na$ [M+Na]$^+$ 735.2, found 735.8.

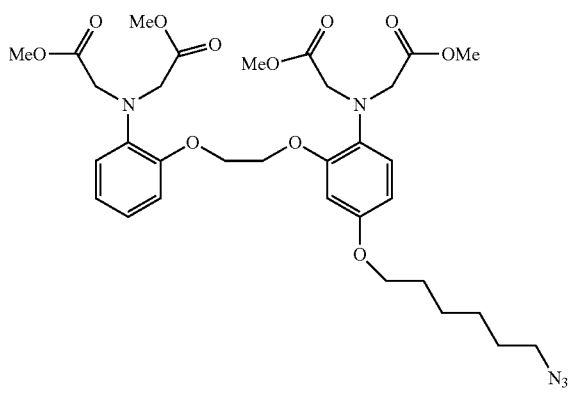

6

To a solution of 5 (3.71 g, 5.218 mmol) in DMF (10 mL) was added NaN$_3$ (1.02 g, 15.65 mmol, 3 eq). The solution was stirred at 80° C. overnight. The product was extracted with EtOAc and washed with water (3 times) and brine (2 times), the organic phase was dried over MgSO$_4$, filtered and concentrated to give 3.52 g of 6 (quant) as a yellowish syrup. $^1$H-NMR (300 MHz, CDCl$_3$): δ 6.84-6.73 (m, 5H), 6.39 (d, J=2.5 Hz, 1H), 6.31 (dd, J=8.7, 2.5 Hz, 1H), 4.19 (d, 4H, $\underline{CH_2}O$), 4.08 (s, 4H, 2$\underline{CH_2}N$), 4.01 (s, 4H, 2$\underline{CH_2}N$), 3.81 (t, J=6.4 Hz, 2H, $\underline{CH_2}O$), 3.48 (d, J=7.3 Hz, 12H, 4 OMe), 3.20 (t, J=6.8 Hz, 2H, $\underline{CH_2}N_3$), 1.70-1.64 (m, 2H, $\underline{CH_2}$), 1.60-1.51 (m, 2H, $\underline{CH_2}$), 1.38 (m, 4H, 2 $\underline{CH_2}$). Impurities between 2 and 3 ppm could not be removed. MS (ES+), calcd for $C_{32}H_{44}N_5O_{11}$ [M+H]$^+$ 674.3, found 674.3. HRMS (ES+), calcd for $C_{32}H_{44}N_5O_{11}$ [M+H]$^+$ 674.3032, found 674.3054.

7

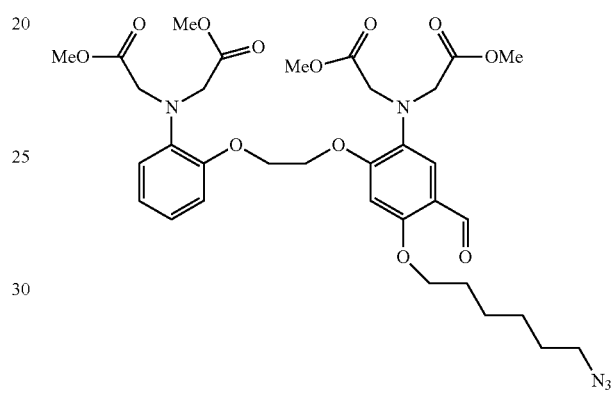

To a solution of 6 (1.22 g, 1.81 mmol) in DMF (5 mL) was added POCl$_3$ (1.35 mL, 14.48 mmol, 8 eq) dropwise without cooling. After addition the solution was allowed to stir for 40 min and then water (50 mL) was added followed by slow addition of a saturated solution of NaHCO$_3$ to reach a pH of 8. The product was extracted with DCM and washed twice with brine before being dried over MgSO$_4$ filtrated and evaporated. The crude was purified by column chromatography on silica gel (Cyclohexane/EtOAc: 6/4) to give 505 mg of 7 (40%) as a yellow syrup. Rf=0.25 (Cyclohexane/EtOAc, 5/5). $^1$H-NMR (300 MHz, CDCl$_3$): δ 10.23 (s, 1H, CHO), 7.27 (s, 1H, Ha), 6.86-6.75 (m, 4H, Hd, He, Hf, Hg), 6.39 (s, 1H, Hc), 4.26 (d, J=2.4 Hz, 4H, 2$\underline{CH_2}O$), 4.06 (d, J=3.3 Hz, 4H, 2$\underline{CH_2}N$), 4.02 (d, J=5.8 Hz, 4H, 2$\underline{CH_2}N$), 3.96 (t, J=6.3 Hz, 2H, $\underline{CH_2}O$), 3.49 (2s, 12H, 2 OMe), 3.22 (t, J=6.8 Hz, 2H, $\underline{CH_2}N_3$), 1.77 (t, J=7.1 Hz, 2H, $CH_2$), 1.57 (t, J=7.0 Hz, 2H, $CH_2$), 1.45-1.35 (m, 4H, $CH_2$). $^{13}$C-NMR (75 MHz, CDCl$_3$): δ 187.99 (CHO), 171.94 ($\underline{C}OOMe$), 171.64 ($\underline{C}OOMe$), 158.88 (Cq Ar), 157.35 (Cq Ar), 150.21 (Cq Ar), 139.40 (Cq Ar), 133.40 (Cq Ar), 122.44 (CH Ar), 121.86 (CH Ar), 119.19 (CH Ar), 118.28 (Cq Ar), 118.07 (Ca), 113.45 (CH Ar), 97.79 (Cc), 68.93 ($\underline{CH_2}O$), 67.53 ($\underline{CH_2}O$), 66.81 ($\underline{CH_2}O$), 53.36 (2$\underline{CH_2}N$), 53.32 (2$\underline{CH_2}N$), 51.69 (OMe), 51.65 (OMe), 51.35 ($CH_2N_3$), 30.19 ($CH_2$), 29.07 ($CH_2$), 28.82 ($CH_2$), 26.92 ($CH_2$), 26.50 ($CH_2$), 25.70 ($CH_2$). MS (ES+), calcd for $C_{33}H_{44}N_5O_{12}$ [M+H]$^+$ 702.3, found 702.2. HRMS (ES+), calcd for $C_{33}H_{44}N_5O_{12}$ [M+H]$^+$ 702.2981, found 702.3008.

The position of the carbonyl was confirmed by further NMR investigations using a HMBC (Heteronuclear Multiple Bond Correlation) experiment.

Numbering for X-Rhodamines

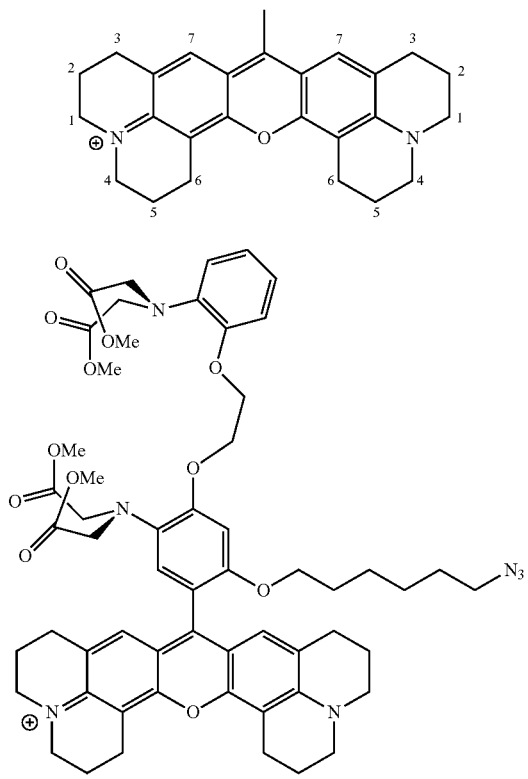

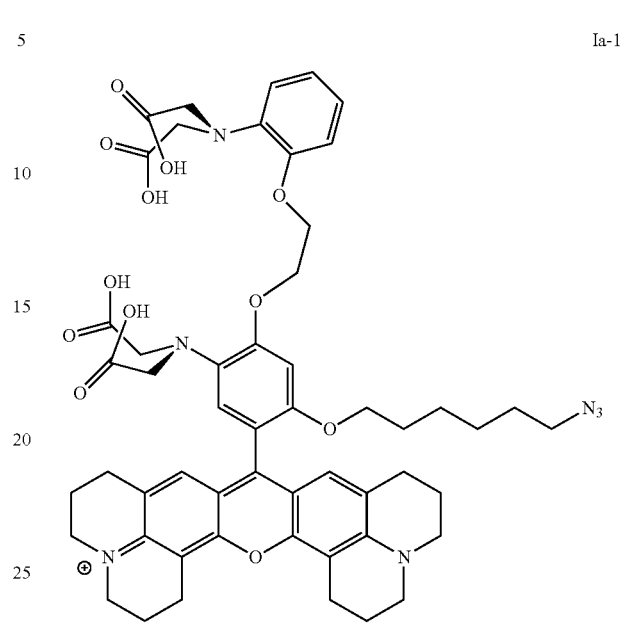

To a solution of aldehyde 7 (300 mg, 0.428 mmol) in propionic acid (5 mL) was added 8-hydroxyjulolidine (161 mg, 0.856 mmol, 2 eq) and PTSA (8 mg, 0.042 mmol, 0.1 eq). The solution was protected from light and stirred at room temperature overnight. To the brown mixture was added a solution of chloranil (103 mg, 0.428 mmol, 1 eq) in DCM (10 mL), the reaction turned dark and was allowed to stir overnight at room temperature. The dark purple solution was evaporated to dryness. The residue was purified by column chromatography on silica gel (gradient of 100% DCM to 9/1 DCM/Methanol) to obtain 130 mg of 8 (30%) as a purple solid after lyophilisation (dioxane/water: 1/1). Rf=0.32 (DCM/MeOH, 9/1). $^1$H-NMR (300 MHz, CDCl$_3$): δ 7.84 (d, J=8.1 Hz, 1H, H Ar), 7.06 (d, J=7.9, 1H, H Ar), 6.97-6.86 (m, 5H, H Ar, H$_7$), 6.71 (d, J=2.9 Hz, 1H, H Ar), 4.47-4.40 (m, 4H, CH$_2$O), 4.21 (s, 4H, NCH$_2$COOMe), 4.11 (s, 4H, NCH$_2$COOMe), 3.87 (t, J=6.1 Hz, 2H, CH$_2$O), 3.67 (s, 6H, 2 OMe), 3.56 (m, 14H, 2 OMe, H$_1$, H$_4$), 3.11 (d, J=7.0 Hz, 2H, CH$_2$N$_3$), 3.04 (t, J=6.3 Hz, 4H, H$_6$), 2.75 (q, J=6.2 Hz, 4H, H$_3$), 2.13-2.10 (m, 4H, H$_5$), 2.00 (t, J=5.5 Hz, 4H, H$_2$), 1.49-1.34 (m, 4H, CH$_2$), 1.19-1.03 (m, 4H, CH$_2$). $^{13}$C-NMR (75 MHz, CDCl$_3$): δ 171.97 (CO ester), 171.56 (CO ester), 153.04 (C Ar), 152.74 (C Ar), 152.31 (C Ar), 152.09 (C Ar), 151.02 (C Ar), 150.43 (C Ar), 144.79 (C Ar), 139.41 (C Ar), 138.16 (C Ar), 132.61 (C Ar), 128.20 (CH Ar), 127.15 (CH Ar), 126.33 (CH Ar), 123.34 (C Ar), 122.64 (CH Ar), 122.61 (CH Ar), 121.91 (CH Ar), 119.54 (CH Ar), 113.89 (C Ar) (CH Ar), 113.43 (C Ar), 113.35 (C Ar), 105.16 (C Ar), 69.10 (CH$_2$O), 67.70 (CH$_2$O), 67.19 (CH$_2$O), 53.66 (NCH$_2$COOMe), 53.52 (NCH$_2$COOMe), 51.73 (4 OMe), 51.16 (CH$_2$N$_3$), 50.97 (C$_1$ or C$_4$), 50.52 (C$_1$ or C$_4$), 28.82 (CH$_2$), 28.73 (CH$_2$), 27.72 (C$_3$), 26.26 (CH$_2$), 25.52 (CH$_2$), 20.83 (C$_2$), 20.00 (C$_6$), 19.85 (C$_5$). MS (ES+), calcd for C$_{57}$H$_{68}$N$_7$O$_{12}$ [M]$^+$1042.5, found 1042.9. HRMS (ES+), calcd for C$_{57}$H$_{68}$N$_7$O$_{12}$ [M]$^+$1042.4920, found 1042.4949.

To a solution of 8 (100 mg, 0.090 mmol) in methanol (6 mL) were added, KOH (504 mg, 9.00 mmol, 100 eq) followed by 2 mL of water, the mixture was stirred overnight. The solution was diluted with aq HCl (1M) and extracted with CHCl$_3$ until the aqueous phase became slightly pink. The organic phase was then dried over MgSO$_4$, filtered and concentrated. The residue was purified on a reverse phase column C-18 using acetonitrile (0.1% TFA) and water (0.1% TFA) mixture as eluant (20% acetonitrile to 60%). The solvents were evaporated and 80 mg of Ia-1 (~90%) were obtained as a purple solid after lyophilisation (dioxane/water, 1/1). MS (ES+), calcd for C$_{53}$H$_{60}$N$_7$O$_{12}$ [M]$^+$986.4, found 986.4. HRMS (ES+), calcd for C$_{53}$H$_{60}$N$_7$O$_{12}$ [M]$^+$986.4294, found 1042.4329.

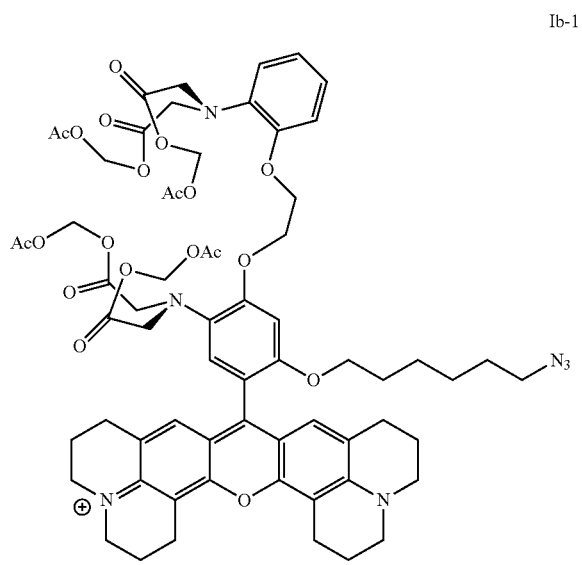

To a solution of Ia-1 (50 mg, ~50 μmol) in chloroform were added bromomethyl acetate (80 μL, 500 μmol, 1 eq) and NEt$_3$ (60 μL, 400 μmol, 8 eq). The solution was protected from light and allowed to stir at room temperature overnight. The reaction was monitored by TLC (DCM/MeOH, 9/1). The solvents were evaporated and the crude was purified by column chromatography on silica gel (gradient of 100% DCM to 9/1 DCM/Methanol) to obtain 30 mg of Ib-1 (~45%) as a purple solid after lyophilisation (dioxane/water, 1/1). Rf=0.45 (DCM/MeOH, 9/1). MS (ES+), calcd for $C_{65}H_{76}N_7O_{20}$ [M]$^+$1274.5, found 1274.5. HRMS (ES+), calcd for $C_{65}H_{76}N_7O_{20}$ [M]$^+$1274.5140, found 1274.5128.

I.3. Synthesis of Dextran Conjugates Ia-1-Dextran

Dextran 6,000 MW (Sigma-Aldrich, ref: 31388) and dextran 1,500 MW (Sigma-Aldrich, ref: 31394) were propargylated as described by Nielsen et al. (Nielsen et al., *Biomacromolecules*, 2010, 11, 1710-1715). The $^1$H-NMR showed that the functionalized dextrans were propargylated once evry glucose unit.

Final MW Dextran 6,000: ~9,800 g·mol$^{-1}$
Final MW Dextran 1,500: ~2,400 g·mol$^{-1}$ Conjugation of Dextran 6,000.

To a solution of propargylated dextran 6,000 (30 mg, ~3 μmol) in water (3 mL) was added Ia-1 (8 mg, 8 μmol, 2.6 eq) in methanol (1 mL) and an heterogeneous solution of CuSO$_4$.5H$_2$O (4 mg, 16 μmol, 5.3 eq) and sodium ascorbate (4 mg, 20 μmol, 6.6 eq) in water (500 μL). The solution was allowed to stir in the dark at room temperature overnight. The solvents were evaporated and the residue was dissolved in 1 mL of EDTA solution (0.1 M) and eluted through a G-25 column (eluant water) to give 24 mg of Ia-1-Dextran 6,000 conjugate (~60% yield).

Conjugation of Dextran 1,500.

To a solution of propargylated dextran 1500 (30 mg, ~12.5 μmol) in DMF (1 mL) was added Ia-1 (4.5 mg, 4.5 μmol, 0.3 eq) in DMF (200 μL) and a heterogeneous solution of CuSO$_4$.5H$_2$O (4 mg, 16 μmol, 1.3 eq) and sodium ascorbate (4 mg, 20 μmol, 1.6 eq) in water (100 μL). The solution was allowed to stir in the dark at 50° C. overnight. The solvents were evaporated and the residue was dissolved in 1 mL of EDTA solution (0.1 M) and eluted through a G-25 column (eluant water to give 20 mg of Ia-1-Dextran 1,500 conjugate (~58% yield).

I.4. Synthesis of compound Ic-1 (n° 17 below) and Ic-2 (n° 18 below)

Scheme 3.

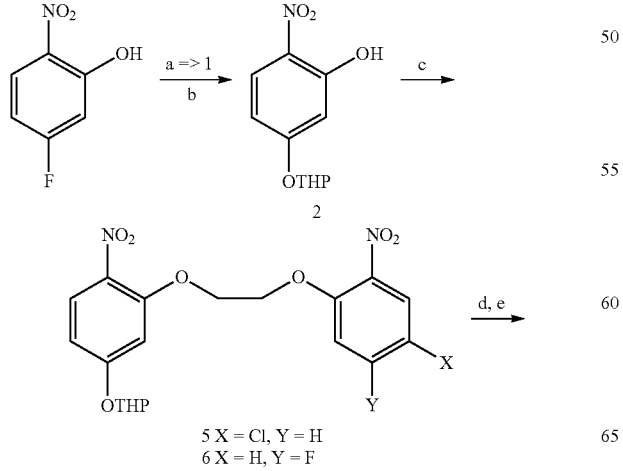

5 X = Cl, Y = H
6 X = H, Y = F

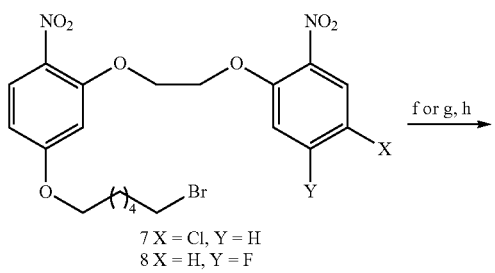

7 X = Cl, Y = H
8 X = H, Y = F

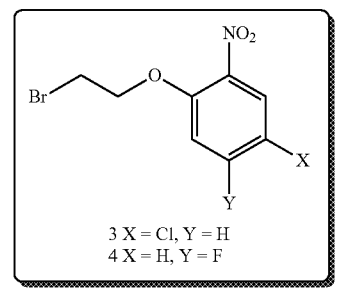

3 X = Cl, Y = H
4 X = H, Y = F

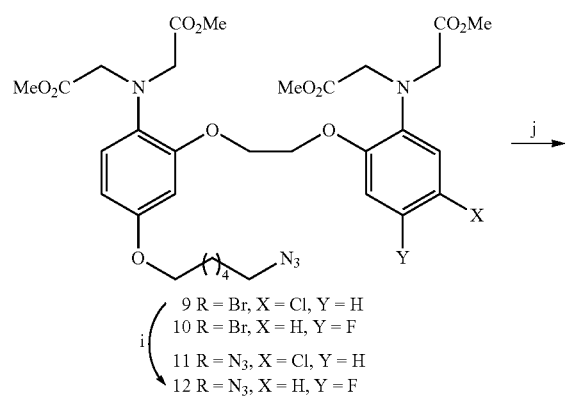

9 R = Br, X = Cl, Y = H
10 R = Br, X = H, Y = F
11 R = N$_3$, X = Cl, Y = H
12 R = N$_3$, X = H, Y = F

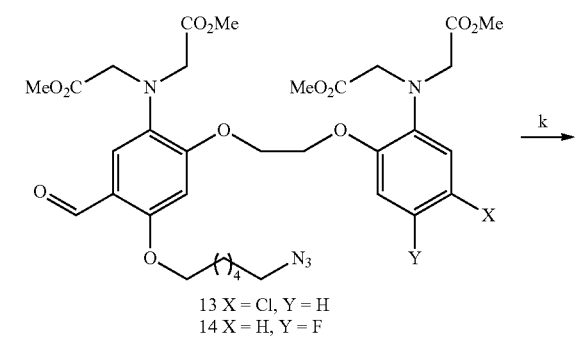

13 X = Cl, Y = H
14 X = H, Y = F

-continued

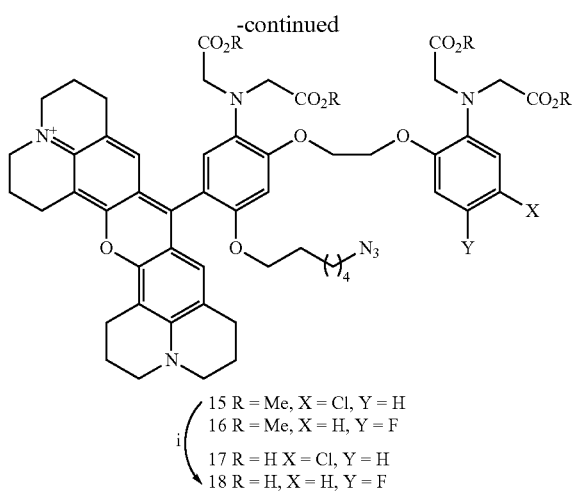

15 R = Me, X = Cl, Y = H
16 R = Me, X = H, Y = F
17 R = H, X = Cl, Y = H
18 R = H, X = H, Y = F

Reagents and Conditions:
a KOH (5 equiv), water, 90-100° C., 93%;
b 3,4-dihydropyran (2.5 equiv), camphorsulfonic acid (0.05 equiv), DCM, 0° C., 86%;
c 3 or 4 (1.1 equiv), K₂CO₃ (1.5 equiv), DMF, 70° C., 85% for 5, 81% for 6;
d Conc. HCl, THF, rt;
e 1,6-dibromohexane (3 equiv), K₂CO₃ (3 equiv), DMF 70° C., 59% for 7, 83% for 8 over two steps;
f With substrate 7: SnCl₂·2H₂O (8 equiv), conc. HCl, EtOH, 80° C.;
g With substrate 8: H₂, Pd/C, AcOEt/MeOH (4:1), rt;
h BrCH₂CO₂Me (12-15 equiv), DIEA (12-15 equiv), acetonitrile, 80° C., 48% for 9, 42% for 10 over two steps;
i NaN₃ (3 equiv), DMF, 80° C., 92% for 11, 97% for 12;
j Vilsmeier reagent (3 equiv), DMF, 60° C., 55% for 13, 56% for 14;
k 8-hydroxyjulolidine (2 equiv), TfOH (0.15-0.3 equiv), DCM, rt, then p-chloranil (1 equiv), rt, 43% for 15, 39% for 16;
l 10M KOH, MeOH, rt, 40% for 17, 77% for 18.

HCl, THF, rt; (e) 1,6-dibromohexane (3 equiv), K₂CO₃ (3 equiv), DMF, 70° C., 59% for 7, 83% for 8 over two steps; (f) With substrate 7: SnCl₂.2H₂O (8 equiv), conc. HCl, EtOH, 80° C.; (g) With substrate 8: H₂, Pd/C, AcOEt/MeOH (4:1), rt; (h) BrCH₂CO₂Me (12-15 equiv), DIEA (12-15 equiv), acetonitrile, 80° C., 48% for 9, 42% for 10 over two steps; (i) NaN₃ (3 equiv), DMF, 80° C., 92% for 11, 97% for 12; (j) Vilsmeier reagent (3 equiv), DMF, 60° C., 55% for 13, 56% for 14; (k) 8-hydroxyjulolidine (2 equiv), TfOH (0.15-0.3 equiv), DCM, rt, then p-chloranil (1 equiv), rt, 43% for 15, 39% for 16; (l) 10 M KOH, MeOH, rt, 40% for 17, 77% for 18.

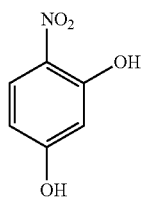

1

To a solution of potassium hydroxide (42.9 g, 764 mmol) in water (150 mL) was added portionwise 5-fluoro-2-nitrophenol (24.0 g, 153 mmol). The mixture was heated at 90° C. for 24 h then the temperature was raised up to 100° C. After refluxing for 19 h, the orange solution was cooled to room temperature then diluted in water and washed with aq. 1M HCl. The aqueous layer was extracted with ethyl acetate then the combined organic layers were washed with brine then dried over MgSO₄, filtered and concentrated to afford 1 (22 g, 93%) as a pale orange solid.

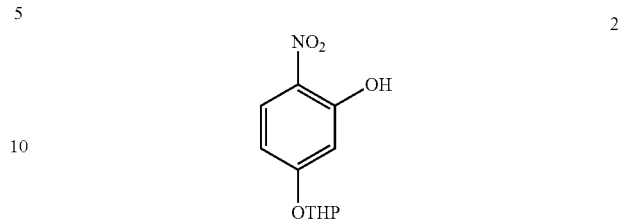

2

A solution of 1 (4.75 g, 30.64 mmol) and 3,4-dihydropyran (7 mL, 76.61 mmol) in CH₂Cl₂ (150 mL) was cooled to 0° C. then camphorsulfonic acid (0.355 g, 1.53 mmol) was added. The yellow solution was stirred at 0° C. for 20 min then triethylamine (0.300 mL) was added and the mixture was concentrated. The residue was taken up in CH₂Cl₂ (50 mL) then hexanes (400 mL) was added in order to precipitate the product. After 2 h at room temperature then 2 days at −18° C., the solid was filtered then purified by flash chromatography (cyclohexane/ethyl acetate 95:5 to 92:8) to afford 2 (6.29 g, 86%) as a yellow solid.

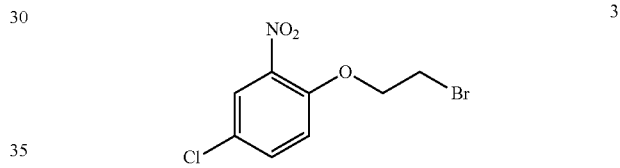

3

To a solution of 4-chloro-2-nitrophenol (20 g, 0.115 mmol) in N,N-dimethylformamide (100 mL) was added 1,2-dibromoethane (50 mL, 576 mmol) then potassium carbonate (32 g, 230 mmol). The mixture was heated at 70° C. for 2 h 30, cooled to room temperature then diluted with ethyl acetate and filtered through a celite pad. The filtrate was concentrated to dryness then taken up in ethyl acetate, washed with brine and dried over MgSO₄, filtered and concentrated. The residue was purified by flash chromatography (cyclohexane/ethyl acetate 9:1 to 85:15) to afford 3 (21.6 g, 67%) as a yellowish solid.

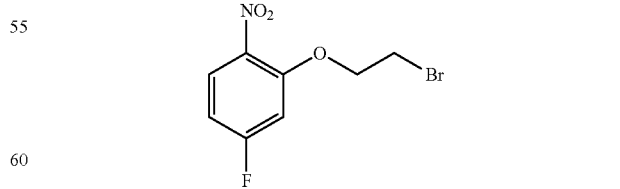

4

5-fluoro-2-nitrophenol (10.3 g, 65.56 mmol) was treated following the procedure which gave 3 to afford 4 (9.91 g, 57%) as a yellowish solid after flash chromatography (cyclohexane/ethyl acetate 9:1 to 85:15).

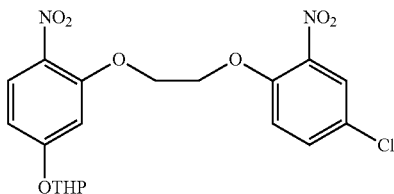

5

To a solution of 2 (3.86 g, 16.14 mmol) and 3 (4.98 g, 17.75 mmol) in N,N-dimethylformamide (20 mL) was added potassium carbonate (3.34 g, 24.2 mmol). The mixture was heated overnight at 70° C. then cooled to room temperature, diluted in ethyl acetate and filtered through a celite pad. The filtrate was concentrated to dryness then the residue was taken up in ethyl acetate and washed with aq. 1M HCl. The aqueous layer was extracted with ethyl acetate then the combined organic layers were washed with brine then dried over MgSO$_4$, filtered and concentrated. The residue was recrystallized from ethyl acetate/petroleum ether then the solid was filtered off and washed with cold petroleum ether to afford 5 (6.04 g, 85%) as a yellow solid.

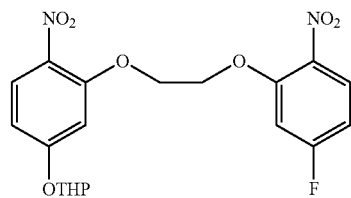

6

Compounds 2 (5.38 g, 22.49 mmol) and 4 (6.53 g, 24.74 mmol) were treated following the procedure which gave 5 to afford 6 (9.50 g, 81%) as a yellow solid after flash chromatography (cyclohexane/ethyl acetate 9:1 to 4:1).

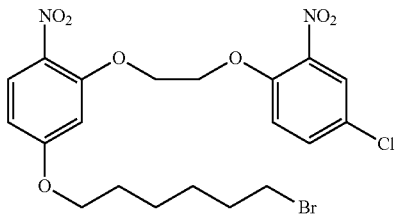

7

To a solution of 5 (6.04 g, 13.76 mmol) in a 2:1 mixture of THF/water (150 mL) was added conc. HCl (15 mL). The solution was stirred at room temperature for 1 h 30 then diluted in ethyl acetate and washed with brine. The aqueous layer was extracted with ethyl acetate then the combined organic layers were dried over MgSO$_4$, filtered and concentrated to dryness.

The residue was dissolved in N,N-dimethylformamide (45 mL) then 1,6-dibromohexane (6.30 mL, 41.28 mmol) and potassium carbonate (2.85 g, 20.64 mmol) were added. The mixture was stirred at 70° C. for 2 h 30 then diluted with ethyl acetate and filtered through a celite pad. The filtrate was concentrated then taken up in CH$_2$Cl$_2$ and washed with aq. 1M HCl. The aqueous layer was extracted with CH$_2$Cl$_2$ then the combined organic layers were washed with brine then dried over MgSO$_4$, filtered and concentrated. The residue was purified by flash chromatography (cyclohexane/ethyl acetate 95:5 to 85:15) then the residue was taken up in ethyl acetate and hexanes (200 mL) was added. After triturating for 10 min then cooling at −25° C. for 1 h, the precipitate was filtered off to afford 7 (4.21 g, 59%) as an off white solid.

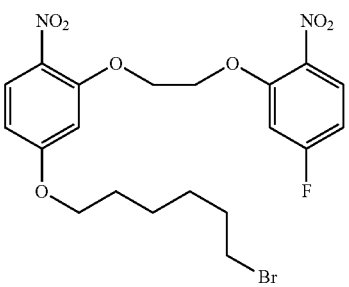

8

Compound 6 (7.52 g, 17.80 mmol) was treated following the procedure which gave 7 to afford 8 (7.36 g, 83%) as a yellowish solid after flash chromatography (cyclohexane/ethyl acetate 9:1 to 4:1) followed by a precipitation from hexanes.

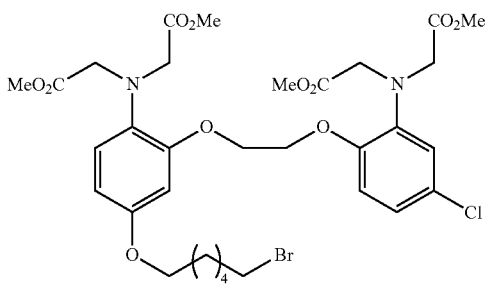

9

To a suspension of 7 (2.59 g, 5.0 mmol) in absolute ethanol (40 mL) was added SnCl$_2$.2H$_2$O (9.0 g, 40 mmol) and conc. HCl (6.5 mL). The mixture was stirred in the dark at 80° C. for 2 h then cooled to room temperature and brought to pH>11 with dropwise addition of aq. 3M NaOH. A grey precipitate started forming and the solution turned gradually from yellow to reddish. The resulting suspension was diluted with water then extracted with diethyl ether (5×100 mL). The combined organic layers were dried over MgSO$_4$, filtered and concentrated to dryness to afford the crude amino derivative as a dark brown oil.

The residue was dissolved in acetonitrile (10 mL) then methyl bromoacetate (7.1 mL, 75 mmol) and N,N-diisopropylethylamine (13.1 mL, 75 mmol) were added. The mixture was stirred in the dark and under argon at 80° C. for 38 h then cooled to room temperature. The mixture was diluted with CH$_2$Cl$_2$ then washed with satd. aq. NaHCO$_3$ and the aqueous layer was extracted with CH$_2$Cl$_2$. The combined organic layers were dried over MgSO$_4$, filtered and concentrated to dryness. The crude residue was purified by flash chromatography (cyclohexane/ethyl acetate 9:1 to 7:3) to afford 9 (1.78 g, 48%) as a brownish syrup.

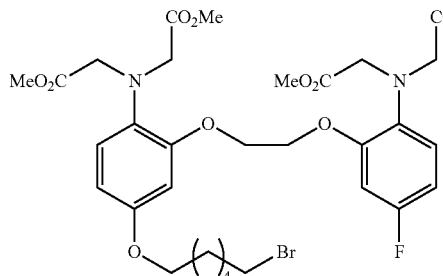

To a solution of 8 (0.490 g, 0.977 mmol) in a 4:1 mixture of ethyl acetate/methanol (10 mL) was added 10% w/w palladium on carbon (0.100 g). The suspension was stirred at room temperature under hydrogen atmosphere for 3 h then filtered through a celite pad. The filtrate was concentrated to dryness to afford the crude amino derivative as a dark brown oil.

The residue was dissolved in acetonitrile (2 mL) then methyl bromoacetate (1.1 mL, 11.7 mmol) and N,N-diisopropylethylamine (2 mL, 11.7 mmol) were added. The mixture was stirred in the dark and under argon at 80° C. for 20 h then cooled to room temperature. The mixture was diluted with CH$_2$Cl$_2$ then washed with satd. aq. NaHCO$_3$ and the aqueous layer was extracted with CH$_2$Cl$_2$. The combined organic layers were dried over MgSO$_4$, filtered and concentrated to dryness. The crude residue was purified by flash chromatography (cyclohexane/ethyl acetate 9:1 to 7:3) to afford 9 (0.301 g, 42%) as a brownish syrup.

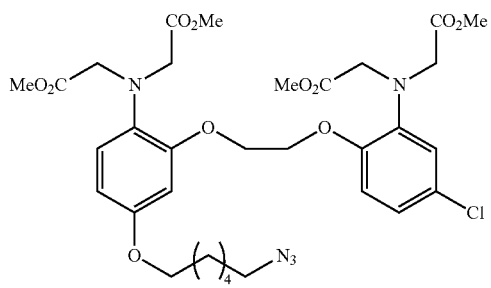

To a solution of 9 (1.02 g, 1.37 mmol) in N,N-dimethylformamide (6 mL) was added sodium azide (0.270 g, 3.06 mmol). The solution was strirred in the dark and under argon at 80° C. for 21 h then cooled to room temperature and diluted with ethyl acetate. After washing twice with water, the combined aqueous layers were extracted with ethyl acetate. The combined organic layers were washed with brine then dried over MgSO$_4$, filtered and concentrated to dryness to afford 11 (0.897 g, 92%) as a brownish syrup.

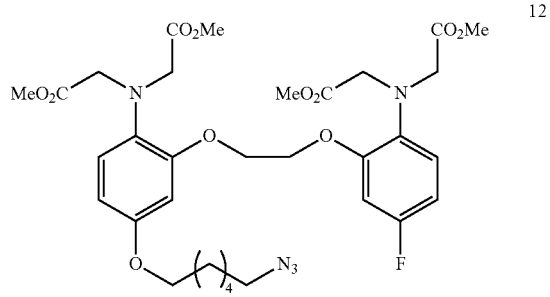

Compound 10 (0.287 g, 0.393 mmol) was treated following the procedure which gave 11 to afford 12 (0.264 g, 97%) as a brownish syrup.

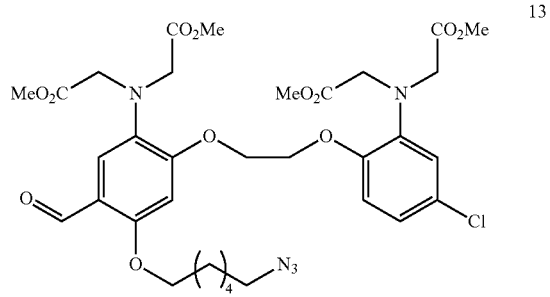

A solution of phosphoryl chloride (0.350 mL, 3.73 mmol) in N,N-dimethylformamide (0.700 mL) was stirred at 0° C. for 1 h then added dropwise to a solution of 11 (0.880 g, 1.24 mmol) in N,N-dimethylformamide (4 mL). The mixture was stirred in the dark at 60° C. for 1 h 30 then cooled to room temperature before diluting with ethyl acetate and adding satd. aq. NaHCO$_3$. The aqueous layer was extracted with ethyl acetate then the combined organic layers were washed with brine, dried over MgSO$_4$, filtered and concentrated. The crude residue was purified by flash chromatography (cyclohexane/ethyl acetate 9:1 to 3:2) to afford 13 (0.506 g, 55%) as an orange syrup.

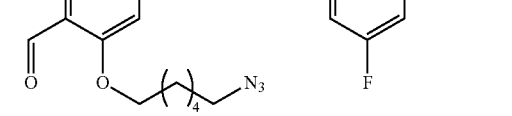

Compound 12 (0.234 g, 0.338 mmol) was treated following the procedure which gave 13 to afford 14 (0.135 g, 56%) as an orange oil after flash chromatography (cyclohexane/ethyl acetate 3:2 to 1:1).

15

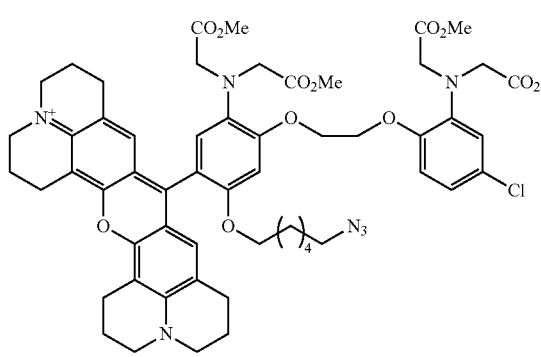

To a solution of 13 (0.110 g, 0.149 mmol) in CH$_2$Cl$_2$ (1 mL) was added 8-hydroxyjulolidine (0.056 g, 0.299 mmol) then trifluoromethanesulfonic acid (4 μL, 0.045 mmol). The solution was stirred overnight in the dark at room temperature then p-chloranil (0.037 g, 0.149 mmol) was added and the brown solution turned dark. After stirring in the dark at room temperature for 4 h, the purple mixture was concentrated. The crude residue was purified by flash chromatography (CH$_2$Cl$_2$/methanol 100:0 to 95:5) to afford 15 (0.075 g, 43%) as a dark purple solid. $^1$H NMR (CD$_3$OD, 300 MHz) δ 6.94 (s, 2H), 6.91-6.80 (m, 4H), 6.60 (td, J=8.2 Hz, J=2.7 Hz, 1H), 4.48-4.36 (m, 4H), 4.12 (s, 4H), 4.10 (s, 4H), 3.92 (t, J=5.7 Hz, 2H), 3.61 (s, 6H), 3.57-3.50 (m, 12H), 3.09-2.99 (m, 6H), 2.84-2.67 (m, 4H), 2.14-2.06 (m, 4H), 2.02-1.94 (m, 4H), 1.47-1.39 (m, 2H), 1.34-1.24 (m, 2H), 1.14-1.04 (m, 2H), 1.02-0.94 (m, 2H); $^{13}$C NMR (CD$_3$OD, 75 MHz) δ 173.5, 173.3 (4C, 4C=O), 154.6, 154.4, 153.7, 153.6, 152.2, 153.0, 152.4, 137.0, 133.8, 128.3, 124.9, 123.7, 121.4, 121.3, 114.6, 114.5, 106.4, 101.3, 70.1, 68.9 (2C), 54.7 (2C), 52.2, 52.1, 51.8, 51.4, 29.9, 29.8, 28.7, 27.2, 26.7, 21.9, 21.0, 20.9.

16

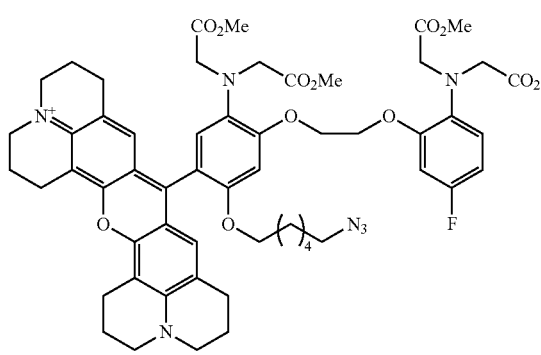

Compound 14 (0.117 g, 0.162 mmol) was treated following the procedure which gave 15 to afford 16 (0.075 g, 39%) as a deep purple solid after flash chromatography (CH$_2$Cl$_2$/methanol 100:0 to 94:6). $^1$H NMR (CD$_3$OD, 300 MHz) δ 6.94 (s, 2H), 6.91-6.80 (m, 4H), 6.60 (td, J=8.2 Hz, J=2.7 Hz, 1H), 4.48-4.36 (m, 4H), 4.12 (s, 4H), 4.10 (s, 4H), 3.92 (t, J=5.7 Hz, 2H), 3.61 (s, 6H), 3.57-3.50 (m, 12H), 3.09-2.99 (m, 6H), 2.84-2.67 (m, 4H), 2.14-2.06 (m, 4H), 2.02-1.94 (m, 4H), 1.47-1.39 (m, 2H), 1.34-1.24 (m, 2H), 1.14-1.04 (m, 2H), 1.02-0.94 (m, 2H); $^{13}$C NMR (CD$_3$OD, 75 MHz) δ 173.5, 173.3 (4C, 4C=O), 154.6, 154.4, 153.7, 153.6, 152.2, 153.0, 152.4, 137.0, 133.8, 128.3, 124.9, 123.7, 121.4, 121.3, 114.6, 114.5, 106.4, 101.3, 70.1, 68.9 (2C), 54.7 (2C), 52.2, 52.1, 51.8, 51.4, 29.9, 29.8, 28.7, 27.2, 26.7, 21.9, 21.0, 20.9.

17

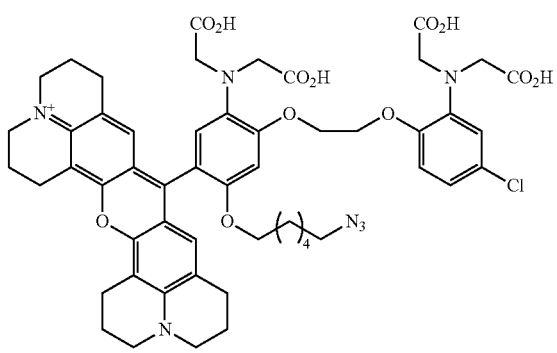

To a solution of 15 (0.114 g, 0.105 mmol) in methanol (7 mL) was added aq. 10 M KOH (1 mL). The mixture was stirred in the dark at room temperature for 20 h then diluted with chloroform and washed with aq. 1 M HCl. The aqueous layer was extracted with chloroform then the combined organic layers were dried over MgSO$_4$, filtered and concentrated. The crude residue was purified on a reverse phase column C-18 using acetonitrile (0.1% TFA) and water (0.1% TFA) as eluant (20% ACN to 60%) to afford 17 (i.e. compound or formula Ic-1) (0.043 g, 40%) as a deep purple solid after lyophilization (water/dioxane 1:1).

MS (ES+): C$_{53}$H$_{59}$ClN$_7$O$_{12}$$^+$: cald 1020.39. Found: 1020.4

18

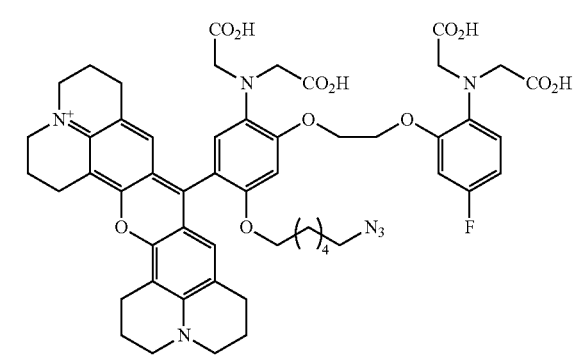

To a solution of 16 (0.055 g, 0.052 mmol) in methanol (4 mL) was added aq. 10 M KOH (0.5 mL). The mixture was stirred in the dark at room temperature for 2 h then diluted with chloroform and washed with aq. 1 M HCl. The aqueous layer was extracted with chloroform then the combined organic layers were dried over MgSO$_4$, filtered and concentrated. The residue was taken up in a 1:1 mixture of water/dioxane then freeze-dried to afford 18 (i.e. compound or formula Ic-2) (0.040 g, 77%) as a deep purple solid.

MS (ES+): C$_{53}$H$_{59}$FN$_7$O$_{12}$$^+$ cald: 1004.42. Found: 1004.3

II. Optical Properties of Compound Ia-1 and Derivatives Thereof

II.1. Absorption and Emission Spectra

Figure 2:
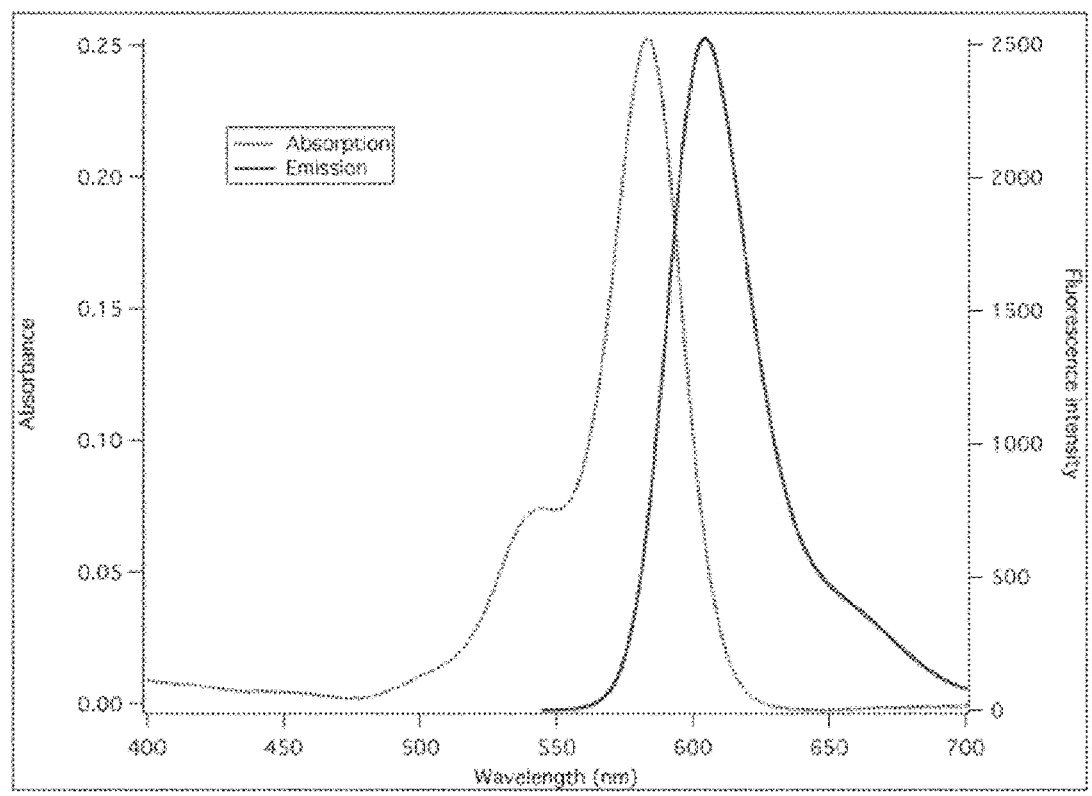
FIG. 2: Normalized absorption and emission spectra of Ia-1 (5 µM in water, 30 mM MOPS, 100 mM KCl, pH 7.2).
Figure 3:
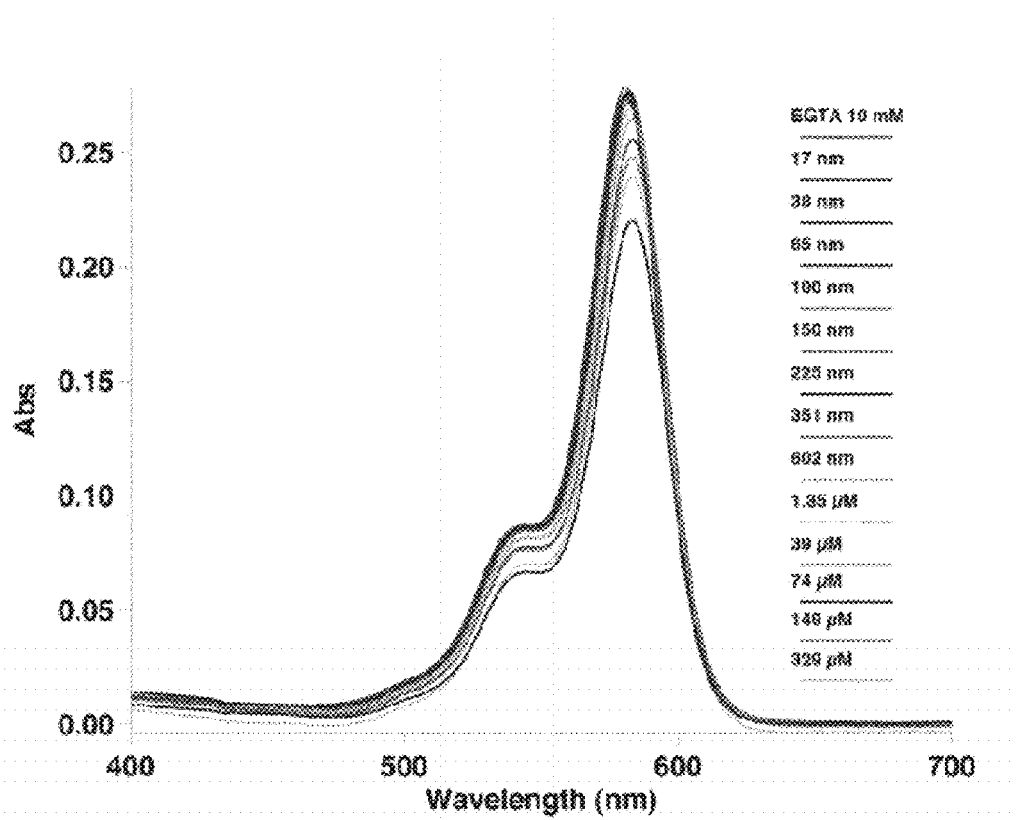
FIG. 3: Absorption spectra of Ia-1 (5 µM) in presence of different concentration of calcium (30 mM MOPS, 100 mM KCl, pH 7.2).
Figure 4:
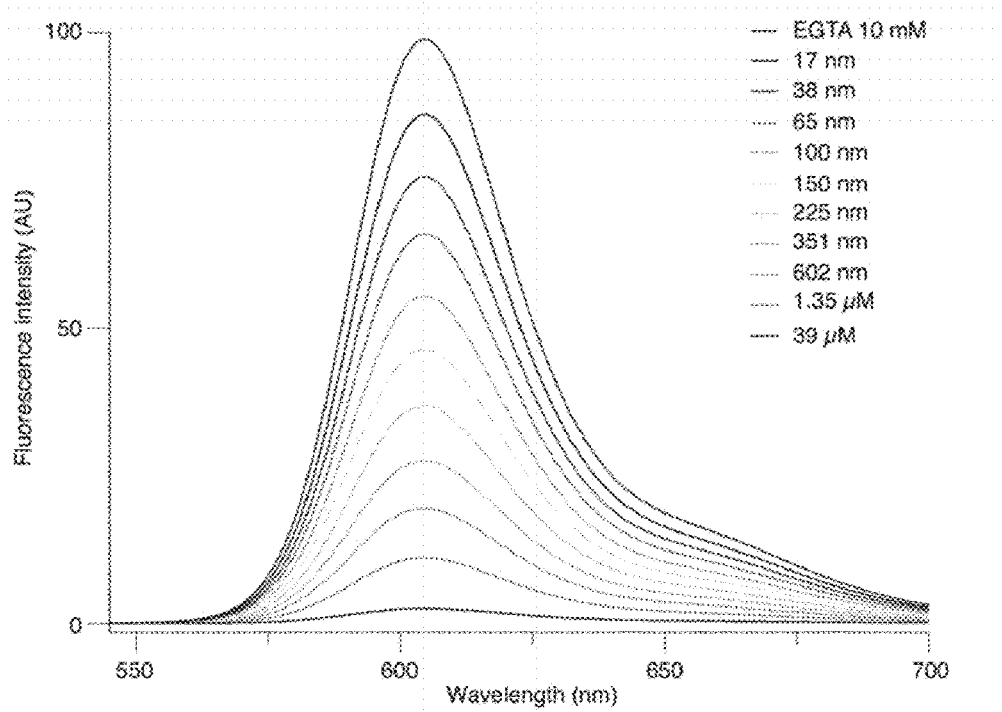
FIG. 4: Emission spectra of Ia-1 (5 µM) in presence of different concentration of calcium (30 mM MOPS, 100 mM KCl, pH 7.2).

Normalised absorption and emission spectra of Ia-1 (5 μM in water, 30 mM MOPS, 100 mM KCl, pH 7.2) were determined and are reported in FIG. 2. Absorption and emission spectra of Ia-1 (5 μM) in presence of different concentration of calcium (30 mM MOPS, 100 mM KCl, pH 7.2) were also determined and are represented in FIGS. 3 and 4 respectively.

II.2. Determination of Dissociation Constants

Figure 5:
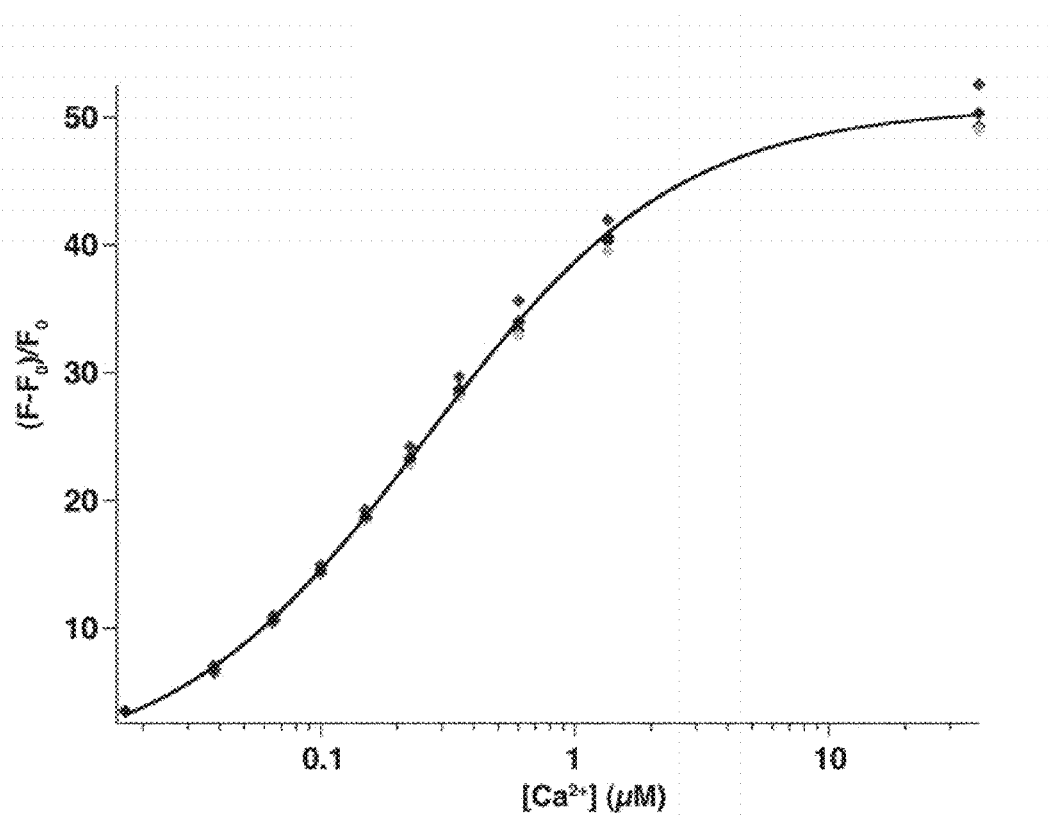
FIG. 5: Fluorimetric titration of Ia-1 (5 µM) against $Ca^{2+}$ in a buffer containing (in mM) 100 KCl and 30 MOPS (pH 7.2).

A fluorimetric titration of Ia-1 (5 μM) against $Ca^{2+}$ in a buffer containing (in mM) 100 KCl and 30 MOPS (pH 7.2) was performed. The resulting curve of titration is reported in FIG. 5. The line fits a Hill profile from the average of three independent titrations and gave an apparent dissociation constant of 258 nM.

Figure 6:
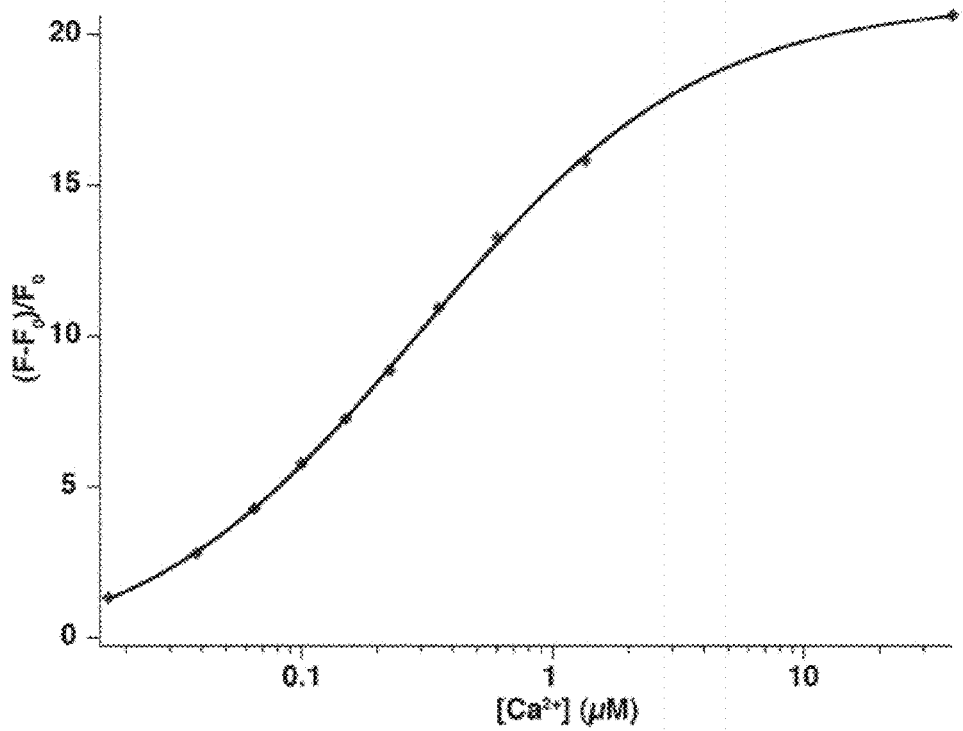
FIG. 6: Fluorimetric titration of Ia-1-Dextran-6000 conjugate against $Ca^{2+}$ in a buffer containing (in mM) 100 KCl and 30 MOPS (pH 7.2).

A fluorimetric titration of Ia-1-Dextran-6000 conjugate against $Ca^{2+}$ in a buffer containing (in mM) 100 KCl and 30 MOPS (pH 7.2) was also conducted. The resulting curve of titration is reported in FIG. 6. The line hit Hill profile and gave an apparent dissociation constant of 295 nM.

Figure 7:
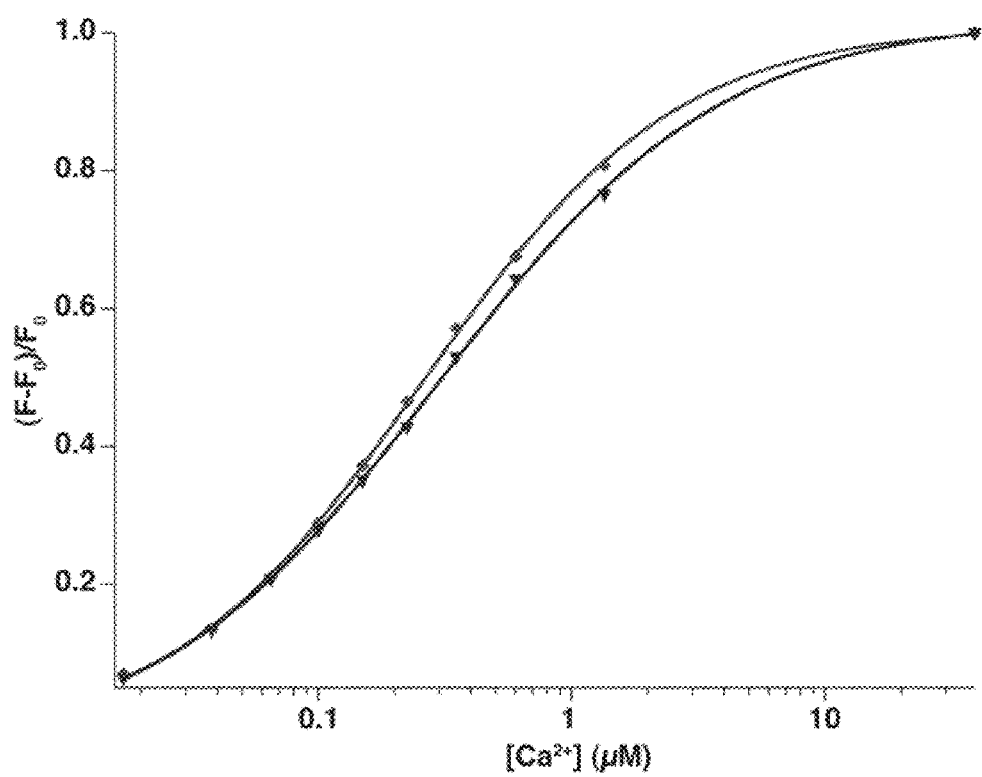
FIG. 7: Normalised fluorimetric titrations against $Ca^{2+}$ of Ia-1 (diamond points) and its dextran-6000 conjugate Ia-1-Dextran-6000 (triangular points).

The normalised fluorimetric titrations against $Ca^{2+}$ of Ia-1 and its dextran-6000 conjugate Ia-1-Dextran-6000 are represented in FIG. 7.

Figure 13:
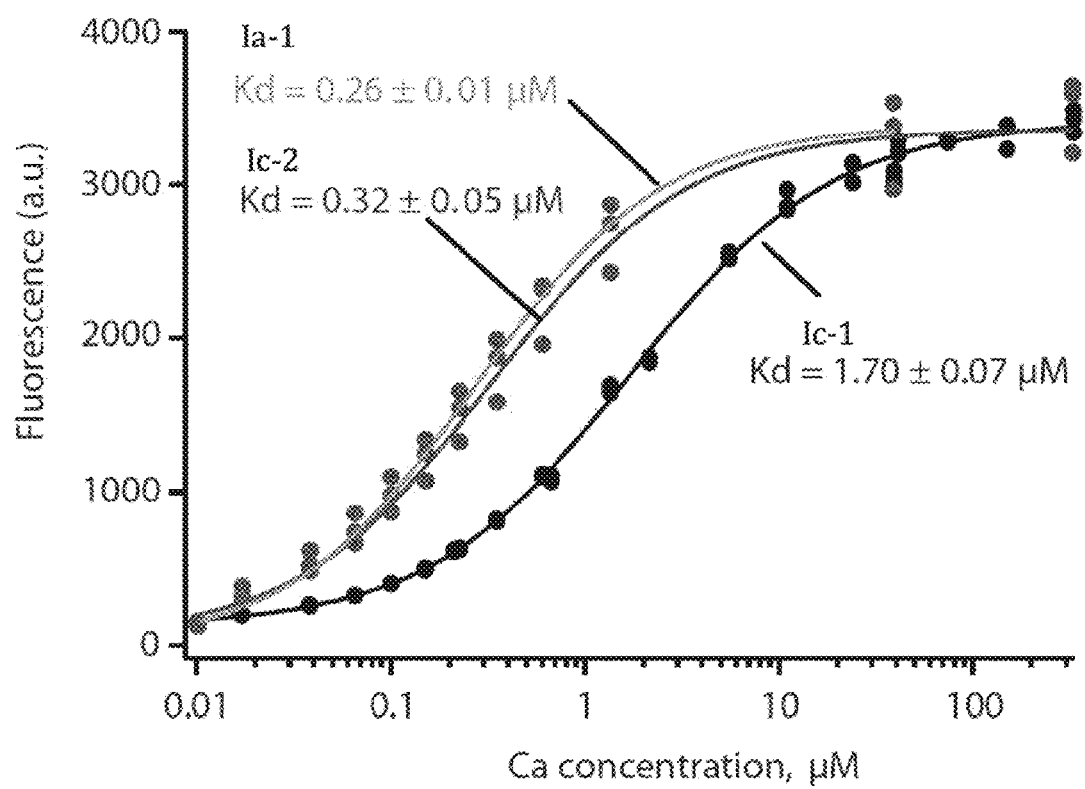
FIG. 13: Normalised fluorimetric titrations against $Ca^{2+}$ of Ia-1, Ic-1 and Ic-2.

A fluorimetric titration of Ic-1 and Ic-2 against $Ca^{2+}$ in a buffer containing (in mM) 100 KCl and 30 MOPS (pH 7.2) was also conducted. The line hit Hill profile and gave an apparent dissociation constant of 1.70 μM for Ic-1 and 0.32 μM for Ic-2. The normalised fluorimetric titrations against $Ca^{2+}$ of Ia-1, Ic-1 and Ic-2 are represented in FIG. 13.

II.3. Determination of the Quantum Yield
Determination of Ia-1 Fluorescence Quantum Yields.

The quantum yields φ of Ia-1 were calculated from the slope of the integrated spectral emission (545 to 700 nm) of Ia-1 in the presence (2 mM) or absence (0 mM, 10 mM EGTA) of $Ca^{2+}$ vs. absorbance at 535 nm using rhodamine 101 (φ=1.0 in absolute ethanol) as a reference standard. A solvent correction was applied for the comparison of the fluorescence quantum yields of Ia-1 and rhodamine 101. The quantum yields φ were calculated using the following equation where φ is the quantum yield, s is the value of the observed slope and η is the refractive index of the solvent used.

$$\varphi = \varphi_{ref} \frac{s}{s_{ref}} \cdot \frac{\eta^2}{\eta_{ref}^2}$$

The calculations gave: $\varphi_{Calcium\ free}=0.0089$
$\varphi_{Ca2+}=0.4541$

II.4. Two-Photon Excitation of Compound Ia-1

Figure 8:
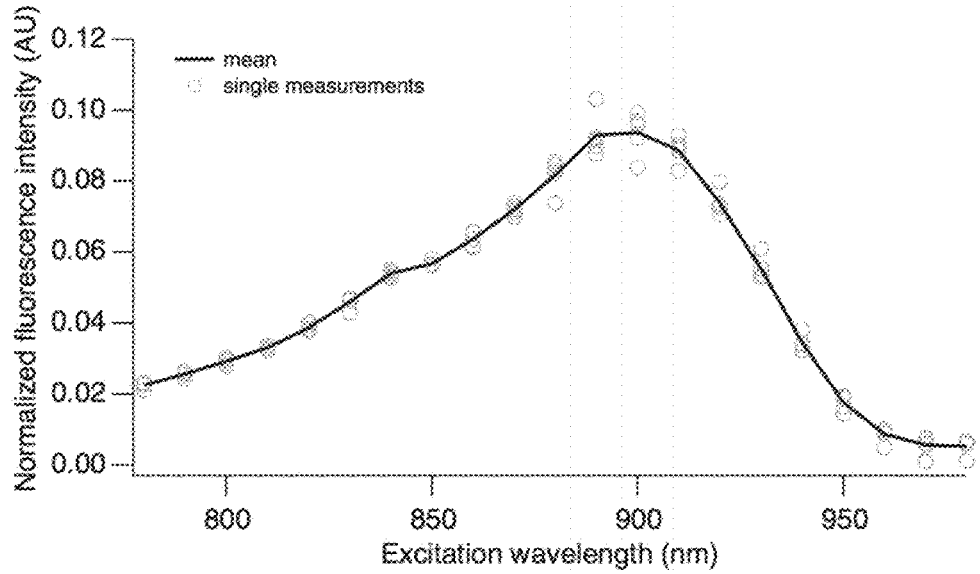
FIG. 8: Two-photon excitation of Ia-1. a) Two-photon excitation spectrum, average of five independent measurements. The individual measurements are indicated by grey circles. b) Plot of fluorescence intensity vs. excitation power. The individual measurements are indicated by grey circles; power function fit to the data (black line).
Figure 8:
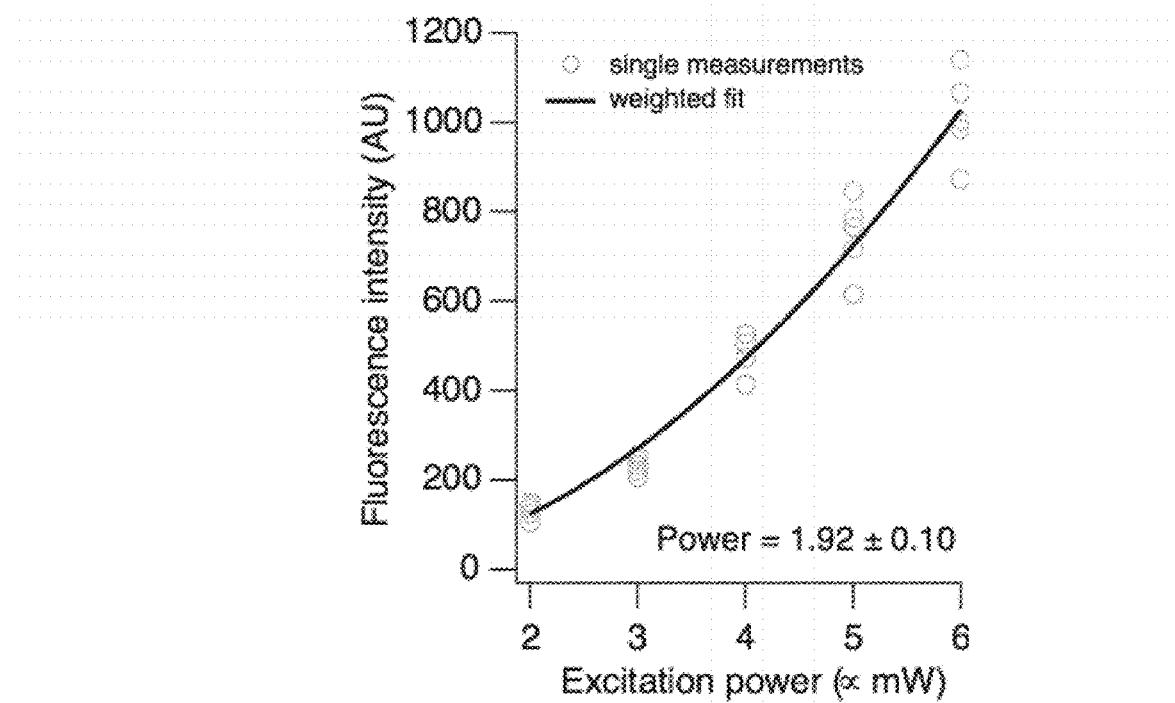

Experiments of two-photon excitation of Ia-1 were conducted. Results are represented on FIG. 8. The power function fit to the data gives a power of 1.92±0.10—within one SD of 2.0, as expected for two-photon excitation evidencing that the measured fluorescence was indeed two-photon excited.

III. Ex Vivo and In Vivo Evaluation
III.1. Material and Methods
Animals

All procedures were approved by the local ethical review committee and performed under license from the UK Home Office in accordance with the Animal (Scientific Procedures) Act 1986. For in vivo preparations, analgesics (Carprofen) were provided as needed.

Slicing

Parasagittal cerebellar slices (200 μm) were made using standard techniques from C57BL6/J mice (Harlan) at postnatal days 25-29. Artificial CSF (ACSF) for both slicing and recording contained the following (in mM): 125 NaCl, 2.5 KCl, 26 $NaHCO_3$, 1.25 $NaH_2PO_4$, 25 glucose, 1 $MgCl_2$, and 2 $CaCl_2$, and was bubbled with 5% carbon dioxide, 95% oxygen. Slices were continuously superfused with ACSF during the experiment. Slice experiments were performed at room temperature.

For high speed imaging experiments, acute 260 μm thick slices were obtained from the cerebellar vermis of P60 mice and superfused with extracellular saline medium.

Electrophysiology and Imaging in Cerebellum

Full frame and linescan two-photon imaging was performed using microscopes optimized for in vitro (Prairie Technologies) or in vivo (MOM, Sutter) experiments. Two photon excitation was provided by a pulsed Ti:Sa laser (MaiTai HP, Newport), tuned to a central wavelength of 890 to 920 nm. The microscopes were controlled by ScanImage 3.5 and 3.7.1. Patch-clamp pipettes were filled with an internal solution containing (in mM): K-methanesulfonate 133, KCl 7, HEPES 10, Mg-ATP 2, $Na_2$ATP 2, $Na_2$GTP 0.5, EGTA 0.05, 0.1 Alexa Fluor 488 and Ia-1-Dextran as indicated; pH 7.2. Recordings from visually identified Purkinje cells were made using a Multiclamp 700B amplifier (Molecular Devices). Data were lowpass filtered at 4 kHz and acquired at 20 kHz using an ITC-18 digitizer (Instrutech) controlled by AxoGraph X (http://www.axographx.com/). Electrical stimuli were delivered via a theta-glass bipolar electrode filled with ACSF using a constant current stimulus isolator (DS-3, Digitimer). When using electrical stimulation, 10 μM SR-95531 (Sigma or Tocris) was added to the perfusion medium.

Climbing fiber stimulation-evoked transient $[Ca^{2+}]$ changes in Purkinje cell spines were recorded at high acquisition rate (>2 kHz) by two-photon random-access microscopy, a technique is based on the use of acousto-optic deflectors (AODs), which enable selective scanning of defined points. Purkinje cells were recorded in current-clamp mode, using 2-3MΩ patch pipettes containing 300 μM Ia-1. Recordings were obtained by use of a Multiclamp 700B (Molecular Devices). Following the dialysis of Ia-1, Purkinje cells in slices were imaged under a 25× Leica water immersion objective (HCX IRAPO L 25×/0.95). Two-photon excitation was produced by a pulsed Ti:Sa laser (Chameleon Vision Plus, Coherent) coupled into the transmitted light pathway of the microscope by a dichroic filter (740dcsx, Chroma Technology Corporation) and tuned to a central wavelength of 890 nm. A custom-made user interface based on National Instrument cards programmed under Labview was used to operate the AODs and coordinate the scanning protocols and signal acquisition. A multifunction card (NI-PCI-MIO 16 E-4) was used to pass all the triggers necessary to synchronize the imaging and the electrophysiology and to control the piezo-electric device that moves the objective in Z. Fluorescence photons were detected by cooled AsGaP photomultipliers (H7421-40, Hamamatsu) discriminated and counted on a fast digital card.

Virus Injection

Young (P19) C57BL6/J mice were anesthetized using isoflurane, an incision was made into the scalp and a small (~0.5 mm) craniotomy was performed over lobule V of the cerebellar vermis. A widebore (~50 μm) micropipette containing viral suspension (AAV1.hSyn.iGluSnFr.WPRE.SV40, University of Pennsylvania Vector Core) was inserted through the craniotomy and carefully lowered 1.0 mm into the brain. Using application of low pressure 400-800 nL viral suspension were slowly injected (10-20 minutes). After the injection further 5-10 minutes were waited before retraction of the injection pipette. The scalp was glued and sutured and the mouse left to recover. At least 7 days incubation time were allowed prior to further experiments.

In Vivo Imaging of Olfactory Sensory Neuron Terminals

Kv3.1-eYFP mice (8-10 week-old) were anesthetized with an intraperitoneal injection of ketamine (100 mg/kg) and xylazine (10 mg/kg). Ia-1-Dextran-6000 was dissolved 2.5% w/v in a solution of aCSF (in mM: 125 NaCl, 2.5 KCl, 1.25 $NaH_2PO_4$, 25 $NaHCO_3$, 1 $MgCl_2$, 2 $CaCl_2$ and 25 glucose) with 0.2% Triton X-100 (Sigma-Aldrich). 8 µl of this solution was injected in the mouse naris, and mice were left on their backs to recover from anesthesia. 7 days later, an acute craniotomy was performed over the dorsal olfactory bulb and the brain stabilized with 3.5% agar for imaging. To activate olfactory sensory neurons (OSNs), odors were applied in a 1 ml/min flux of filtered, humidified air supplemented with 30% oxygen. eYFP and Ia-1 fluorescence was collected in two separate channels ("green" and "red", respectively) of a custom-built two-photon laser scanning microscope, with the femtosecond pulsed excitation beam set to 910 nm.

In Vivo Bulk Loading and Imaging

Adult C57BL6 mice (6-9 weeks; Harlan) were anesthetized with isoflurane, supplemented with 1 mg/kg chlorprothixene. A 1.5-2 mm craniotomy was performed over cerebellar lobule V. Care was taken to leave the dura mater intact. Ib-1 was prepared and injected using standard methods. A 50 µg aliquot was dissolved in 20% Pluronic-127 in DMSO (Invitrogen) and then diluted 1:10 in saline (150 mM NaCl, 2.5 mM KCl, 10 mM HEPES, pH 7.4). This solution was filtered and injected into the cerebellum under visual guidance using a patch-pipette and 500-750 mbar pressure for 1-3 minutes. After injection the preparation was left to incubate for up to 1.5 hours prior to imaging. This helped improve labeling and lower background fluorescence.

Data Analysis and Statistics

Imaging data were analyzed using ImageJ (http://rsbweb-.nih.gov/ij/). Extracted fluorescence traces, linescans and electrophysiological data were analyzed using in house routines programmed in IgorPro versions 5 or 6.2 (Wavemetrics) and in pClamp 10 (Molecular Device Inc).

Figure 9:
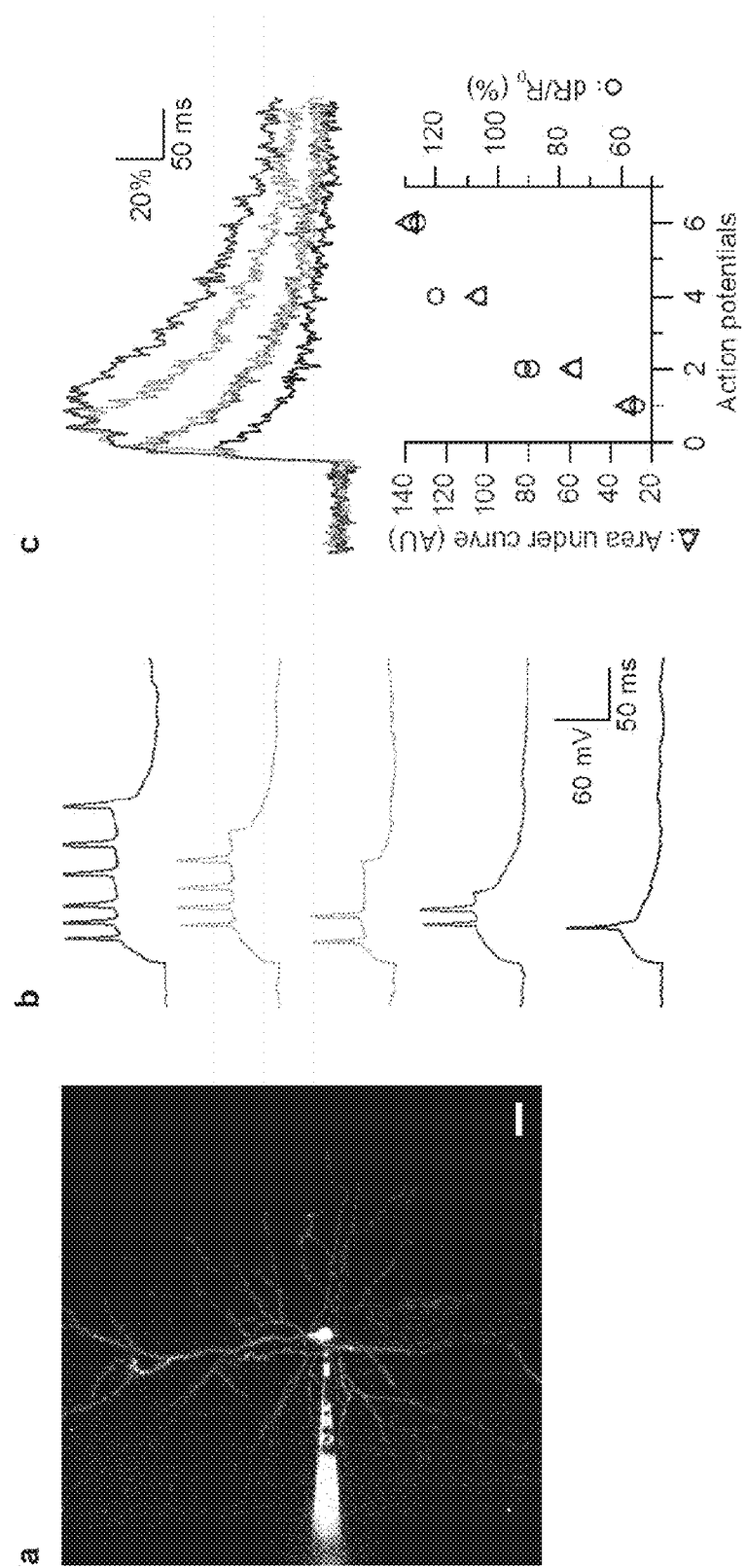
FIG. 9: Imaging $Ca^{2+}$ in layer 2/3 neurons in vivo. a) A layer 2/3 pyramidal neuron filled with Alexa Fluor 488 and Ia-1-Dextran-6000. b) Action potential (AP) c) $Ca^{2+}$ transients.

III.2. In Vivo $Ca^{2+}$ Imaging in Layer 2/3 Pyramidal Neurons $Ca^{2+}$ was imaged in layer 2/3 neurons in vivo as reported in FIG. 9.

FIG. 9a represents a layer 2/3 pyramidal neuron (~200 µm below the brain surface), filled with 100 µM Alexa Fluor 488 and 200 µM Ia-1-Dextran-6000.

FIG. 9b reports action potential (AP) trains evoked by current injection of increasing duration.

The corresponding $Ca^{2+}$ transients were recorded by line-scanning the proximal dendrite (red line in a) at 500 Hz and displayed as percentage change in "red-over-green" ratio from baseline (FIG. 9c). Fluorescence traces are aligned to AP onset and color-coded to match the number of APs (top). The peak amplitudes (circle) and the area under the curve (triangle) of the fluorescence trace were plotted against the number of action potentials (bottom). While the area increases nearly linearly, the peak amplitude saturates, as expected for a high affinity indicator.

III.3. Population Imaging of Purkinje Cells In Vivo Using AM Bulk Loading

Purkinje cells were imaged in vivo using bulk loading of Ia-1. Results are reported in FIG. 10.

FIG. 10a shows the configuration of AM-ester (Ib-1) injection and imaging. FIG. 10b presents the resulting staining of tissue 60 minutes after injection of indicator. Purkinje cells can be seen as vertical stripes with occasional brighter spots (presumably corresponding to dendrites). Active Purkinje cell dendrites identified using a spatial PCA/ICA algorithm are depicted in FIG. 10c.

Fluorescence traces from the identified dendrites are recorded in FIG. 10d. Stimulus timing is indicated by the underlying grey bars. Stimulus triggered averages of the complete traces in d (20 repetitions) is represented in FIG. 10e. Note that all cells except for the third (red) show a stimulus-locked response.

In the past decade, population imaging of neurons using bulk loading of acetoxymethyl ester (AM) derivatives of $[Ca^{2+}]$ indicators has become one of the most common methods to monitoring neuronal activity. This has opened a wide new field of applications for these AM esters. Yet, nearly all recent bulk loading studies rely on either Oregon Green-488 BAPTA-1-AM (OGB-1) or Fluo-4-AM, again limiting the possibility to multiplex indicators for different signalling species. Here the Applicant demonstrates that the AM derivative of Ia-1 (i.e. Ib-1) is a suitable red-emitting alternative to these indicators. A series of three experiments was performed in which Ib-1 was bolus injected in the cerebellar vermis (FIG. 10a). In all experiments, the resulting labelling was comparable to that obtained with OGB-1 in similar conditions. The main difference was the need for a longer incubation period prior to onset of imaging (60-75 minutes compared to 45-60 minutes for OGB-1 and 15-30 minutes for Fluo-4). In all experiments fluorescence traces extracted for identified dendrites (FIG. 10c) showed clear complex spike activity with a good signal-to-noise ratio (FIG. 10d) as expected for this preparation. Using electrocutaneous stimulation of the hind limb it was possible to evoke responses time-locked to the stimulus in a high fraction of dendrites (FIG. 10e). Taken together, these data show that Ib-1 is similarly suited for population imaging experiments as OGB-1 AM or Fluo-4 AM, with the advantage of leaving the green detection channel free for additional indicators.

IV. Discussion

In cuvette calibration experiments (paragraph II.2), Ia-1 was found to have a $K_D$ of 258±8 nM, with a 50-fold (±2) increase of fluorescence on binding $[Ca^{2+}]$ and a maximum quantum yield of 0.45 (paragraph II.3). Besides suitability for single photon excitation, Ia-1 is also effectively two-photon excited (paragraph II.4).

To minimize the subcellular compartmentalization typical for red emitting fluorescent probes, 1.5 and 6 kD dextran conjugates were obtained by click chemistry and used in the further experiments.

Figure 11:
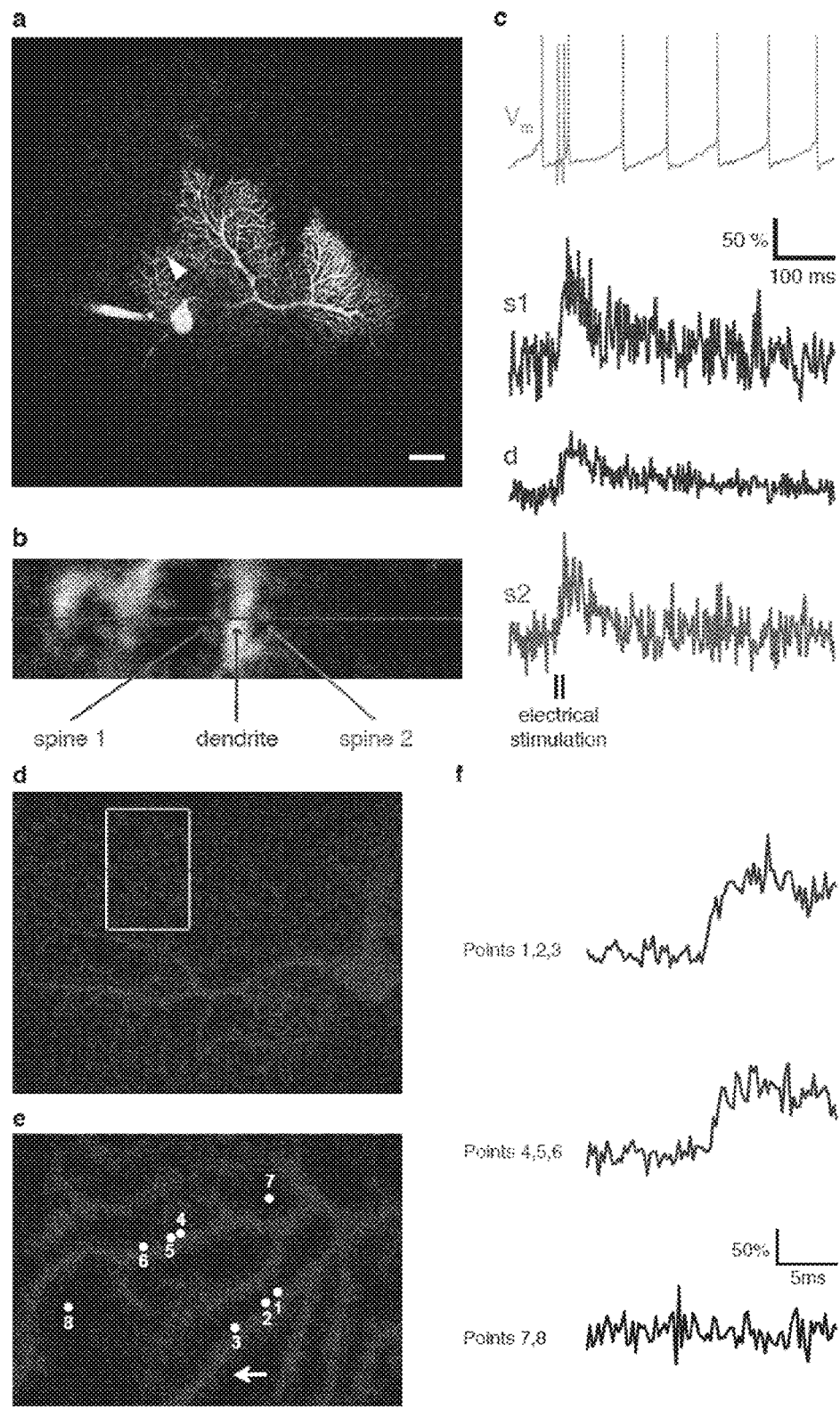
FIG. 11: [$Ca^{2+}$] transients in cerebellar slices imaged with Ia-1. a-c) Parallel fiber stimulation. a) Purkinje cell filled with 100 µM Alexa Fluor 488 and 200 µM Ia-1-Dextran via patch-pipette (scale bar: 25 µm). The white arrow head marks the stimulation site. b) Segment of dendrite showing the region imaged in c using a line scan. c) Voltage trace (top) showing spontaneous spiking of the Purkinje cell with a parallel fiber stimulus evoked increase in spiking frequency. Stimulus evoked $Ca^{2+}$ transients (bottom) at s1, s2 and d, the two spines and the underlying dendritic shaft, respectively (average of three trials). Stimulus timing is indicated at the bottom of the traces. d-f) Climbing fiber stimulation. d) Purkinje cell filled with 300 µM Ia-1, with region of interest indicated by yellow rectangle. e) Region of interest with measurement points indicated. Note that points 1-3 and 4-6 are on different spiny branchlets while points 7 and 8 are in the background. f) $Ca^{2+}$ transients following climbing fiber activation recorded at 2.8 kHz (traces averaged over 26 stimulations).

Using two-photon microscopy and simultaneous patch-clamp recording, it was verified that Ia-1 gives signals comparable to commonly used green emitting $[Ca^{2+}]$ probes. For this purpose, Purkinje cells were filled in cerebellar slices with Ia-1-Dextran-6000 and Alexa Fluor-488 via patch-clamp pipettes (FIG. 11a). Electrical stimulation of parallel fiber inputs to Purkinje cells resulted in an increase in spike frequency and $[Ca^{2+}]$ transients that were recorded using line-scan imaging (FIG. 11b). Even mild stimulation (2 pulses at 100 Hz) yielded large fluorescence transients (>100% $dF/F_0$) with a high signal-to-noise ratio in single spines (FIG. 11c). As reported in previous studies, transients were larger and faster in dendritic spines than in the dendritic shaft.

Next, high-speed random access microscopy (FIG. 11d) was used to verify that Ia-1 reports $[Ca^{2+}]$ transients with kinetics comparable to commonly used indicators. During stimulation of the climbing fiber, fluorescence traces were acquired from multiple spines (range: 4 to 14) at rates over 1 kHz (range 2.2 to 4.8 kHz) (FIGS. 11e and 11f). The rise time τ=1.30±0.26 ms (exponential fit; n=59 spines from 7 cells), was not significantly different from/significantly faster than the kinetics found for Fluo-4.

Having verified the suitability of Ia-1 for in vitro experiments, in vivo patch-clamp recordings were then performed from neocortical layer 2/3 pyramidal neurons in anesthetized mice with concomitant [Ca$^{2+}$] imaging (FIG. 9), showing that spiking activity in these neurons resulted in large fluorescence transients, that showed a linear amplitude vs. spike number relation for low spike numbers, saturating for higher spike numbers, as expected for a high affinity calcium indicator. Taken together these experiments demonstrate that Ia-1 is a calcium indicator well suited for a wide range of neuroscience experiments, with a signal quality comparable to previously used high-affinity green emitting probes.

Figure 10:
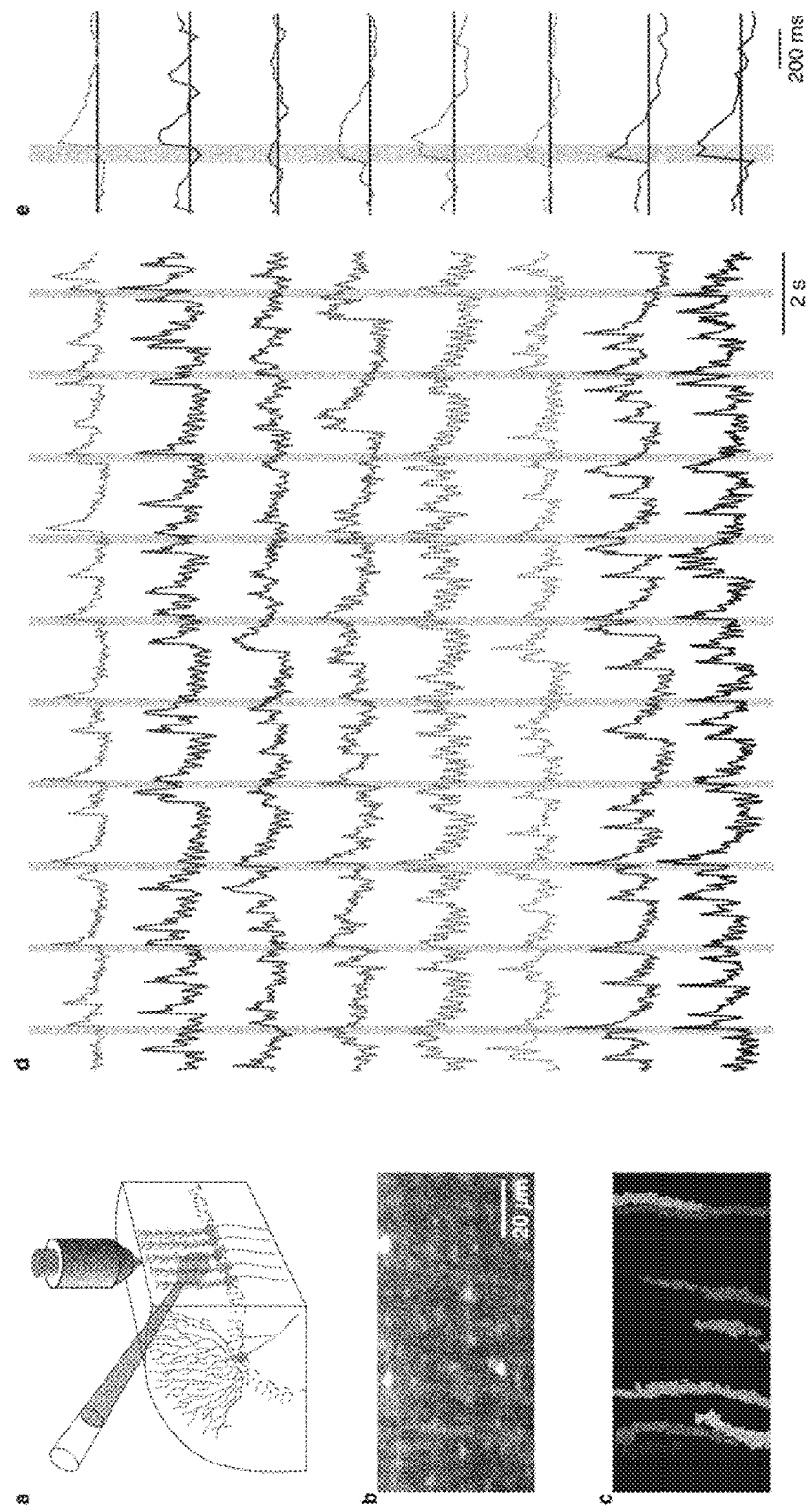
FIG. 10: Imaging Purkinje cells in vivo using bulk loading of Ia-1. a) Configuration of AM-ester (Ib-1) injection and imaging. b) Resulting staining of tissue 60 minutes after injection of indicator. c) Active Purkinje cell dendrites identified using a spatial PCA/ICA algorithm. d) Fluorescence traces from the identified dendrites. e) Stimulus triggered averages of the complete traces in d (20 repetitions).

To complete the functional imaging toolbox, a means of imaging cell populations, rather than single cells is needed. In the past decade this has commonly been achieved using bulk loading of calcium indicators in the AM-ester form (Ib-1). An AM-ester of Ia-1 (i.e. Ib-1) was thus synthesized and used to bulk load cerebellar neurons in vivo (FIG. 10). It was found a labeling identical to that commonly found in experiments using Oregon Green-488 BAPTA-1 AM (OGB-1 AM) as well as comparable spontaneous and sensory evoked responses. This indicates that Ib-1 is a powerful addition to the optophysiological toolbox.

Figure 12:
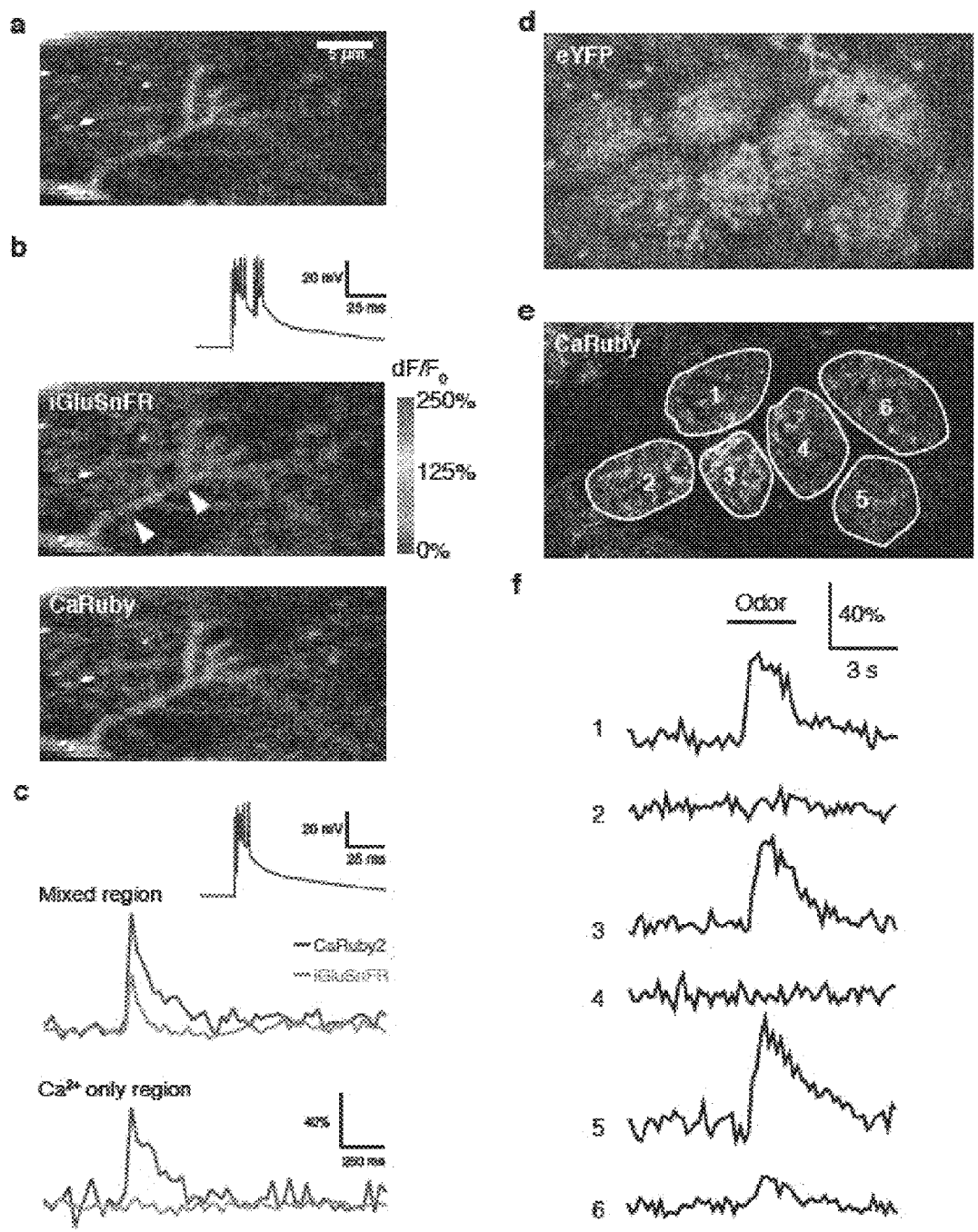
FIG. 12: Dual color functional imaging in vitro and in vivo. a-c) Combined imaging of [Glutamate] and [$Ca^{2+}$] a) A Purkinje cell expressing iGluSnFR was filled with 200 µM Ia-1-Dextran. The image shows the basal fluorescence of Ia-1. b) Double pulse stimulation of the climbing fiber triggers spatially different patterns of glutamate release and $Ca^{2+}$ influx (maximum $dF/F_0$ images; the inset at the top shows the two evoked complex spikes). Note the breaks between regions showing iGluSnFR activation (indicated by white arrows) c) Fluorescence traces for Ia-1 and iGluSnFR following single pulse climbing fiber stimulation (top inset). Note the absence of a fluorescent transient for iGluSnFR in the "$Ca^{2+}$ only" region. d-f) Odor-evoked calcium responses in olfactory bulb glomeruli. d) Juxtaglomerular neurons and mitral cell dendritic tufts expressing YFP demarcate glomeruli in a Kv3.1-eYFP mouse. e) Olfactory sensory neuron glutamatergic terminals, labeled with Ia-1-Dextran, clearly filled the inner boundaries of most glomeruli (Red channel). f) A 3 s application of 30% isoamyl acetate reliably triggered presynaptic calcium responses in several glomeruli.

Making use of the strongly overlapping two-photon excitation spectra of eGFP and Ia-1, a set of experiments was conducted, which were previously not possible: Simultaneous imaging of glutamate release onto Purkinje cells (using iGluSnFR) and the resulting post-synaptic [Ca$^{2+}$] increase (using Ia-1-Dextran-6000). In these experiments acute cerebellar slices of P27-P29 mice were prepared 7 to 9 days after viral transfection of the cerebellar vermis with iGluSnFR. Visually identified Purkinje cells showing green fluorescence were whole-cell recorded and filled with Ia-1-Dextran (FIG. 12a). Electrical stimulation of the glutamatergic climbing fiber input evoked clear fluorescence transients in both color channels (FIG. 12b). We found, glutamate signals to be confined to a distinct subsections of the dendritic (i.e. limited to sites of synaptic release), whereas the resulting [Ca$^{2+}$] transients were global, with comparable amplitudes over different regions in the dendritic tree (FIG. 12c). These experiments demonstrate the potential of two-channel functional imaging, with the red emission and high sensitivity of Ia-1 being an ideal match for numerous other indicators emitting in the green-yellow spectral band.

To verify that dual color imaging is also possible in vivo we used Ia-1-Dextran-6000 to report presynaptic activity in anesthetized Kv3.1-eYFP adult mice. In the olfactory bulb of these mice, mitral and tufted cells, as well as a population of periglomerular neurons, strongly express eYFP and their somata and processes clearly demarcate the external glomerular boundaries (FIG. 12d). Olfactory sensory neuron (OSN) terminals, labeled with Ia-1, filled the inner glomerular boundaries (FIG. 12e). In single glomeruli (n=8 animals) we could record presynaptic calcium responses with an excellent signal to noise ratio. FIG. 12f shows a typical example in which presynaptic calcium responses were selectively evoked by odor presentation in a subset of glomeruli. These responses adapted strongly at this high odorant concentration, as reported previously. These data clearly indicate that Ia-1 can be used in vivo as an efficient red calcium-sensitive dye in the presence of eYFP.

The invention claimed is:
1. A compound of formula I

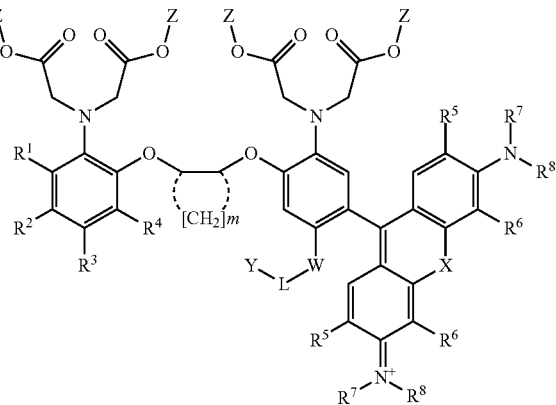

or a salt thereof, wherein
Z represents H, alkyl, CH$_2$—OAc, Na$^+$ or K$^+$;
R$^1$, R$^2$, R$^3$ and R$^4$ represent each independently H, halo, alkyl, COR$^{11}$, OR$^{11}$, SR$^{11}$ or NR$^{11}$R$^{12}$, wherein R$^{11}$ and R$^{12}$ represent each independently H, alkyl or aryl;
m represents 0, 3 or 4;
W represents O, NR$^9$, S or CR$^9$R$^{10}$, wherein R$^9$ and R$^{10}$ represent each independently H or alkyl;
L represents a single bond or a linker selected from the group comprising alkyl, aryl, alkylaryl, arylalkyl, polyethylene glycol (PEG), polypropylene glycol (PPG), peptide, aminocarbonyl, alkylaminocarbonyl, aminothiocarbonyl or a combination thereof; optionally additionally comprising a residue of a reactive group through which L is bounded to Y selected from carbonyl group or triazolo group;
Y represents
a reactive function selected from the group comprising N$_3$, amino, alkylamino, COOH, amide, maleimide, alkyne, SH, OH, ester, N-hydroxysuccinimide ester, N-hydroxyglutarimide ester, maleimide ester, acid anhydride, acid halide, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates and imines; or
a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, biotin, avidin, synthetic polymer, polymeric microparticle, nanoparticle, fluorophore, chromophore, radioisotope, macrocyclic complexes of radioisotope, and combinations thereof;

$R^5$ and $R^6$ each independently represent H, alkyl or halo; $R^7$ and $R^8$ each independently represent H, alkyl; or $R^5$ and $R^7$ are linked together in a single alkyl moiety to form a ring with adjacent carbon and nitrogen atoms; or $R^6$ and $R^8$ are linked together in a single alkyl moiety to form a ring with adjacent carbon and nitrogen atoms; and X represents O, $NR^9$, S, $CR^9R^{10}$, Se or Si, wherein $R^9$ and $R^{10}$ represent each independently H or alkyl.

2. The compounds according to claim 1, wherein, when $R^5$ and $R^7$, or $R^6$ and $R^8$, are linked together in a single alkyl moiety, the single alkyl moiety is propyl.

3. The compound according to claim 1, of formula Ia

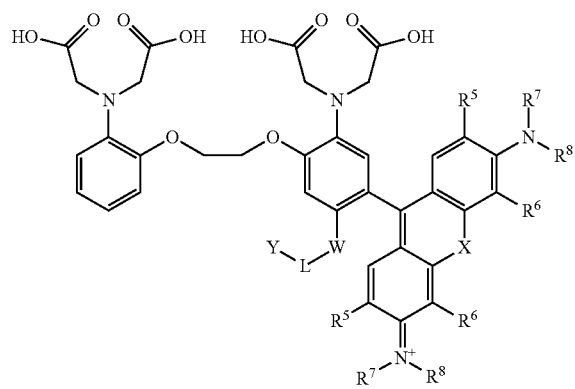

or a salt thereof, wherein W, L, Y, $R^5$, $R^6$, $R^7$, $R^8$ and X are as previously defined.

4. The compound according to claim 1, of formula Ib

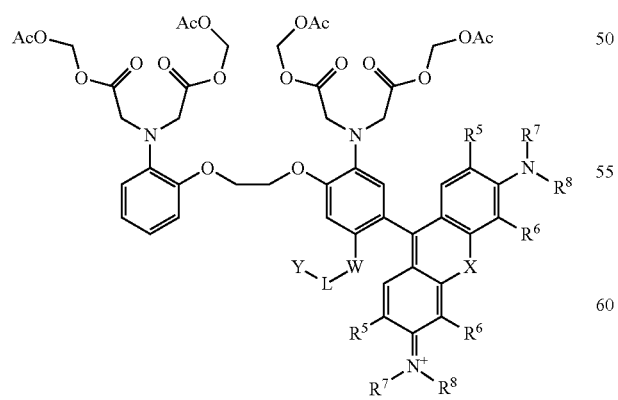

or a salt thereof, wherein W, L, Y, $R^5$, $R^6$, $R^7$, $R^8$ and X are as previously defined.

5. The compound according to claim 1, selected from the group comprising compounds of formula Ia-1, Ia-2 and Ib-1:

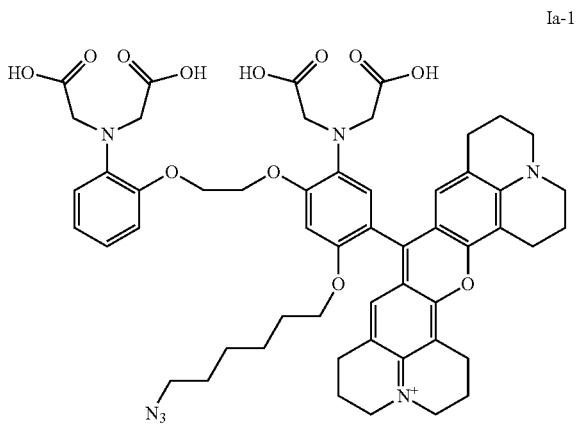

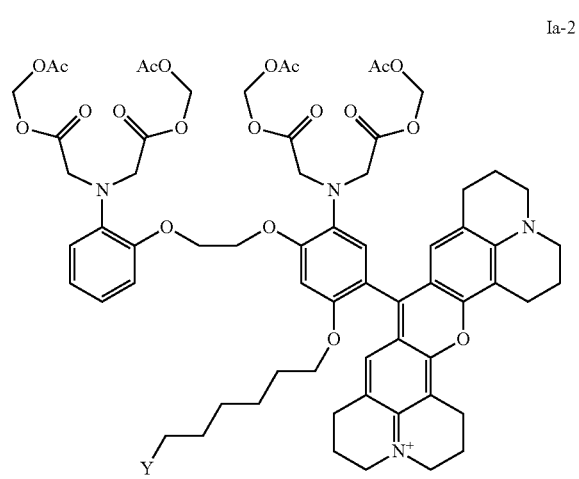

wherein Y represent a dextran bioactive group;

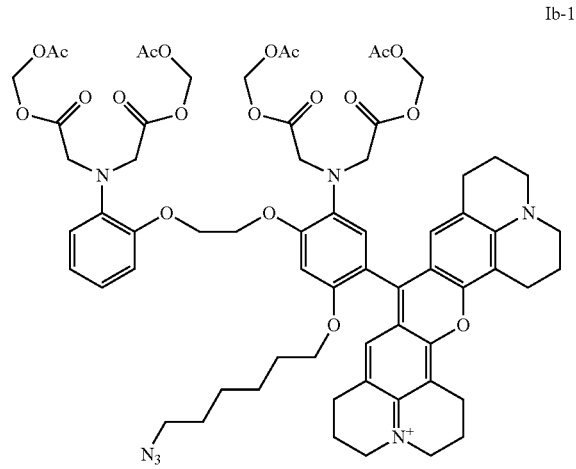

-continued

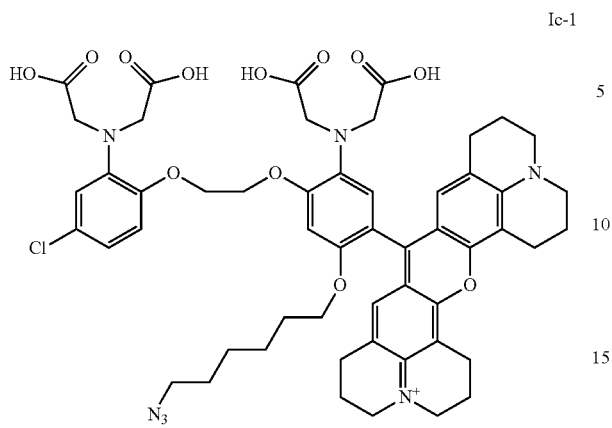

Ic-1

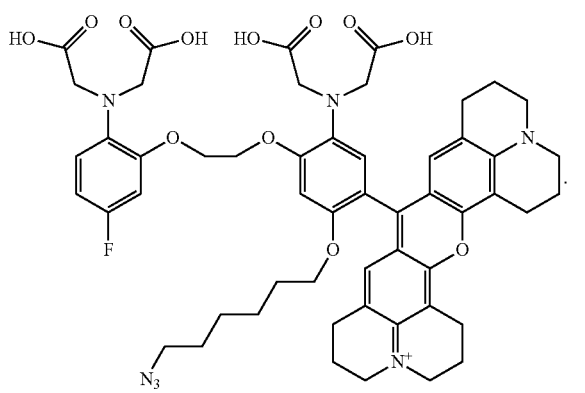

Ic-2

6. Process for manufacturing a compound of formula I according to claim 1, comprising performing a Vilsmeier-Haack reaction on a compound of formula III

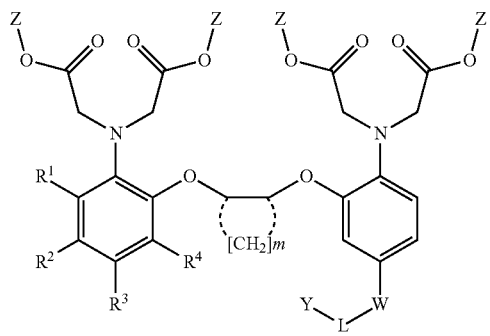

wherein Z, $R^1$, $R^2$, $R^3$, $R^4$, m, W, L and Y are as previously defined;

leading to compound of formula II

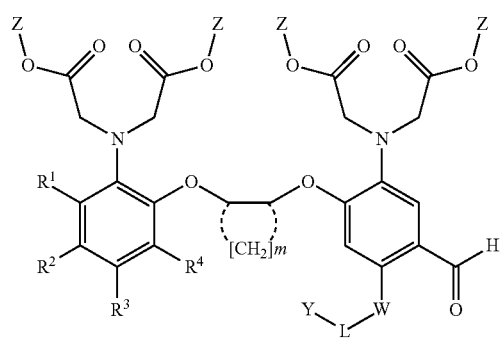

wherein Z, $R^1$, $R^2$, $R^3$, $R^4$, m, W, L and Y are as previously defined;

and further comprising a step of rhodamine formation on the aldehyde function of compound of formula II, to afford compound of formula I.

7. The compound according to claim 2, of formula Ia

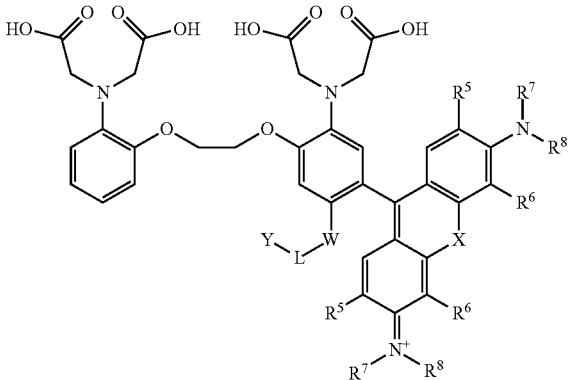

or a salt thereof, wherein W, L, Y, $R^5$, $R^6$, $R^7$, $R^8$ and X are as previously defined.

8. Method of detecting intracellular calcium comprising:
adding a compound according to claim 1 to a sample containing at least one cell;
incubating the sample for a time sufficient for the compound to be loaded into the cell;
illuminating the sample at an exciting wavelength that generates a fluorescent response from the indicator;
detecting the fluorescent response.

9. Method according to claim 8, further comprising:
stimulating the cell;
monitoring changes in the intensity of the fluorescent response from the indicator; and
correlating the changes in fluorescence intensity with changes in intracellular calcium levels.

10. Kit for performing a calcium assay, comprising a compound according to claim 1.

* * * * *